US012658291B2

(12) United States Patent
Wagner et al.

(10) Patent No.: US 12,658,291 B2
(45) Date of Patent: Jun. 16, 2026

(54) SYSTEMS AND METHODS FOR MONITORING USER INTERACTION AND MAINTAINING INTEREST OF A USER

(71) Applicant: ResMed Digital Health Inc., San Diego, CA (US)

(72) Inventors: Stewart Joseph Wagner, Sydney (AU); Sakeena De Souza, Sydney (AU); Andrew William Gillett, Sydney (AU)

(73) Assignee: ResMed Digital Health Inc., San Diego, CA (US)

( * ) Notice: Subject to any disclaimer, the term of this patent is extended or adjusted under 35 U.S.C. 154(b) by 55 days.

(21) Appl. No.: 18/354,016

(22) Filed: Jul. 18, 2023

(65) Prior Publication Data

US 2024/0038343 A1     Feb. 1, 2024

Related U.S. Application Data

(60) Provisional application No. 63/392,851, filed on Jul. 27, 2022.

(51) Int. Cl.
| | | |
|---|---|---|
| *G16H 40/63* | (2018.01) | |
| *G16H 10/60* | (2018.01) | |
| *G16H 40/40* | (2018.01) | |

(52) U.S. Cl.
CPC ............. *G16H 10/60* (2018.01); *G16H 40/40* (2018.01); *G16H 40/63* (2018.01)

(58) Field of Classification Search
CPC ......... G16H 10/60; G16H 40/40; G16H 40/63
See application file for complete search history.

(56) References Cited

U.S. PATENT DOCUMENTS

| | | | |
|---|---|---|---|
| 9,358,353 | B2 | 6/2016 | Armitstead et al. |
| 9,910,963 | B2 * | 3/2018 | Ryan ...................... G06Q 10/10 |
| 10,328,219 | B2 | 6/2019 | Rao et al. |
| 10,569,036 | B2 * | 2/2020 | Delangre .......... A61M 16/0069 |
| 11,587,660 | B2 * | 2/2023 | Sysko ................... G06Q 10/10 |
| 2014/0088373 | A1 | 3/2014 | Phillips et al. |

(Continued)

FOREIGN PATENT DOCUMENTS

| | | |
|---|---|---|
| WO | 2008/138040 A1 | 11/2008 |
| WO | 2012/012835 A2 | 2/2012 |

(Continued)

*Primary Examiner* — Thomas D Alunkal
(74) *Attorney, Agent, or Firm* — Nixon Peabody LLP

(57)     ABSTRACT

Methods and systems are disclosed that involve monitoring use by a user of a device, of an application associated with the device, or a combination thereof. The device is configured to provide therapy to the user. The application is configured to provide control of the device, to provide information to the user related to the therapy, or a combination thereof. The methods and systems also involve determining whether one or more milestones associated with an incentive scheme for the user have been satisfied by the use. The incentive scheme relates to continued provisioning of the therapy to the user by the device. The methods and systems also involve unlocking functionality of the device, the application associated with the device, or a combination thereof for the user based on satisfaction of at least one of the one or more milestones.

22 Claims, 12 Drawing Sheets

(56) References Cited

U.S. PATENT DOCUMENTS

| 2015/0088955 | A1* | 3/2015 | Hendrick | ............... H04L 67/10 |
| | | | | 709/201 |
| 2015/0169844 | A1* | 6/2015 | Munafo | ................. G16H 50/70 |
| | | | | 705/2 |
| 2016/0193437 | A1* | 7/2016 | Bao | ................... A61M 16/0051 |
| | | | | 128/203.14 |
| 2017/0311879 | A1* | 11/2017 | Armitstead | ............ G16H 20/40 |
| 2019/0209044 | A1* | 7/2019 | Hess | .................... A61B 5/7475 |
| 2020/0019726 | A1* | 1/2020 | Perecman | ............... G06F 21/40 |
| 2020/0383580 | A1 | 12/2020 | Shouldice et al. | |
| 2022/0007965 | A1 | 1/2022 | Tiron et al. | |

FOREIGN PATENT DOCUMENTS

| WO | 2014/047310 | A1 | 3/2014 |
| WO | 2016/061629 | A1 | 4/2016 |
| WO | 2017/132726 | A1 | 8/2017 |
| WO | 2018/050913 | A1 | 3/2018 |
| WO | 2019/122413 | A1 | 6/2019 |
| WO | 2019/122414 | A1 | 6/2019 |
| WO | 2020/104465 | A2 | 5/2020 |

* cited by examiner

900

MONITOR USE BY A USER OF A DEVICE AND/OR AN APPLICATION — 902

DETERMINE WHETHER ONE OR MORE MILESTONES HAVE BEEN SATISFIED — 904

UNLOCK FUNCTIONALITY BASED ON SATISFACTION OF MILESTONES — 906

SYSTEMS AND METHODS FOR MONITORING USER INTERACTION AND MAINTAINING INTEREST OF A USER

CROSS-REFERENCE TO RELATED APPLICATIONS

This application claims the benefit of, and priority to, U.S. Provisional Patent Application No. 63/392,851 filed on Jul. 27, 2022, which is hereby incorporated by reference herein in its entirety.

TECHNICAL FIELD

The present disclosure relates generally to systems and methods for monitoring user interaction with a device, with an application associated with the device, or a combination thereof for maintaining interest of a user, and more particularly, to systems and methods for incentivizing a user to maintain interest through an incentive scheme.

BACKGROUND

Many users use a device, or an application, or for a period of time but then lose interest in the device, the application, or both. The loss of interest may result in the user no longer using the device, the application, or both. Discontinuing use may not be detrimental to the user because use of the device, the application, or both may be unrelated to the user's wellbeing or health. However, where the device, the application, or both are related to the user's wellbeing or health, such as in the case where the device provides therapy to the user, losing interest and, even more so, stopping use of the device, the application, or both may affect the user's wellbeing.

Many individuals suffer from sleep-related and/or respiratory-related disorders such as, for example, Sleep Disordered Breathing (SDB), which can include Obstructive Sleep Apnea (OSA), Central Sleep Apnea (CSA), other types of apneas such as mixed apneas and hypopneas, Respiratory Effort Related Arousal (RERA), and snoring. In some cases, these disorders manifest, or manifest more pronouncedly, when the individual is in a particular lying/sleeping position. These individuals may also suffer from other health conditions (which may be referred to as comorbidities), such as insomnia (e.g., difficulty initiating sleep, frequent or prolonged awakenings after initially falling asleep, and/or an early awakening with an inability to return to sleep), Periodic Limb Movement Disorder (PLMD), Restless Leg Syndrome (RLS), Cheyne-Stokes Respiration (CSR), respiratory insufficiency, Obesity Hyperventilation Syndrome (OHS), Chronic Obstructive Pulmonary Disease (COPD), Neuromuscular Disease (NMD), rapid eye movement (REM) behavior disorder (also referred to as RBD), dream enactment behavior (DEB), hypertension, diabetes, stroke, and chest wall disorders.

These disorders are often treated using a respiratory therapy system (e.g., a continuous positive airway pressure (CPAP) system), which delivers pressurized air to aid in preventing the individual's airway from narrowing or collapsing during sleep. However, some users find such systems to be uncomfortable, difficult to use, expensive, aesthetically unappealing and/or fail to perceive the benefits associated with using the system. As a result, some users will lose interest in, and stop using, the respiratory therapy system, which equates to no longer maintaining the interest the respiratory therapy system and its manufacturer.

A manufacture of a device, such as a medical device in general and a respiratory therapy system specifically, often develops a corresponding application that aid the user's use of the device. The application can also act as a direct connection between the user and the manufacturer of the device, often providing greater insight into the user for the purpose of improving of therapy through the device. However, even if the user continues use of the respiratory therapy system, the user may lose interest in the application. Ceasing use of the application may cause the user to miss out on valuable insights in the therapy that can only be provided through the application, or personalized control of the therapy that can only be provided through the application, or the like.

The present disclosure is directed to solving these and other problems.

SUMMARY

According to some implementations of the present disclosure, a method includes monitoring use by a user of a device, of an application associated with the device, or a combination thereof. The device is configured to provide therapy to the user. The application is configured to provide control of the device, to provide information to the user related to the therapy, or a combination thereof. The method also includes determining whether one or more milestones associated with an incentive scheme for the user have been satisfied by the use. The incentive scheme relates to continued provisioning of the therapy to the user by the device. The method also includes unlocking functionality of the device, the application associated with the device, or a combination thereof for the user based on satisfaction of at least one of the one or more milestones.

According to at least one implementation of the method, the functionality includes:
i. providing more granular control of the therapy by the device, providing one or more additional features for the therapy provided by the device, or a combination thereof, ii. one or more ways of visualizing existing data on the device, on the application, or a combination thereof, iii. providing access to premium data on the device, on the application, or a combination thereof, iv. changing one or more stylistic appearances of the device, of the application, or a combination thereof; v. providing access to, control over, or a combination thereof one or more other devices through the application; vi. pairing the device with a smartphone of the user to allow the device to receive additional information from the smartphone, the information unlocking further functionality on the device; vii. providing latest news related to the device, the application, the therapy provided by the device, or a combination thereof; and/or viii. accessing software updates for the device, the application, or a combination thereof.

According to at least another implementation of the method, the one or more stylistic appearances of the device include one or more stylistic appearances of a housing of the device, of a user interface of the device, or a combination thereof.

According to at least another implementation of the method, the additional information from the smartphone includes Global Positioning System (GPS) information for automatically setting functionality of the device based on environmental conditions associated with the GPS information.

According to at least another implementation of the method, the device does not have access to the additional information without the pairing of the device with the smartphone.

According to at least another implementation of the method, the application executes on the smartphone, and the additional information includes physiological information of the user determined by the smartphone, user identification information provided by the user through the smartphone, or a combination thereof.

According to at least another implementation of the method, the one or more additional features for the therapy are non-critical features.

According to at least another implementation of the method, the one or more milestones relate to user compliance with respect to usage of the device, usage of the application, or a combination thereof.

According to at least another implementation of the method, the one or more milestones also apply to one or more other user, the method further including comparing satisfaction of the one or more milestones associated with the incentive scheme for the user with satisfaction of the one or more milestones associated with one or more incentive schemes of one or more other users; and providing a reward to the user, at least one of the one or more other users, or a combination based on the comparison and which of the one or more milestones have been satisfied by which of the user and the one or more other users.

According to at least another implementation of the method, further comprising unlocking one or more rewards associated with one or more participating businesses for the user based on satisfaction of the at least one of the one or more milestones.

According to some implementations of the present disclosure, a system includes a memory and a control system. The memory stores machine-readable instructions. The control system includes one or more processors configured to execute the machine-readable instructions to monitor use by a user of a device, of an application associated with the device, or a combination thereof. The device is configured to provide therapy to the user. The application is configured to provide control of the device, to provide information to the user related to the therapy, or a combination thereof. The one or more processors are further configured to execute the machine-readable instructions to determine whether one or more milestones associated with an incentive scheme for the user have been satisfied by the use. The incentive scheme relates to continued provisioning of the therapy to the user by the device. The one or more processors are further configured to execute the machine-readable instructions to unlock functionality of the device, the application associated with the device, or a combination thereof for the user based on satisfaction of at least one of the one or more milestones.

According to some implementations of the present disclosure, a system includes a memory, and a control system. The memory stores machine-readable instructions. The control system includes one or more processors configured to execute the machine-readable instructions perform to any one or a combination of the method steps and implementations disclosed above.

The above summary is not intended to represent each implementation or every aspect of the present disclosure. Additional features and benefits of the present disclosure are apparent from the detailed description and figures set forth below.

Figure 1:
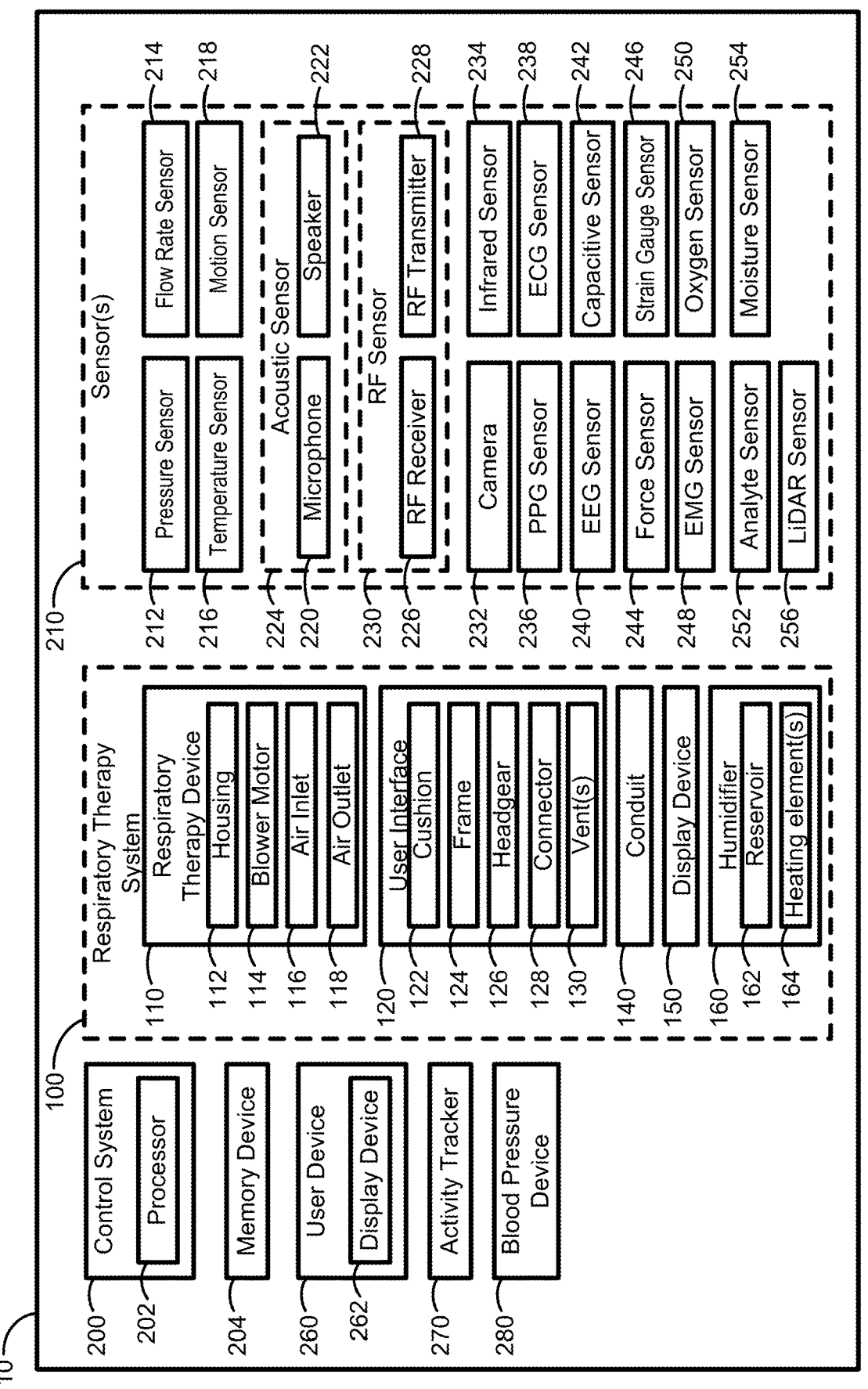
FIG. 1 is a functional block diagram of a system, according to some implementations of the present disclosure.

While the present disclosure is susceptible to various modifications and alternative forms, specific implementations and embodiments thereof have been shown by way of example in the drawings and will herein be described in detail. It should be understood, however, that it is not intended to limit the present disclosure to the particular forms disclosed, but on the contrary, the present disclosure is to cover all modifications, equivalents, and alternatives falling within the spirit and scope of the present disclosure as defined by the appended claims.

DETAILED DESCRIPTION

Many individuals suffer from sleep-related and/or respiratory disorders, such as Sleep Disordered Breathing (SDB) such as Obstructive Sleep Apnea (OSA), Central Sleep Apnea (CSA) and other types of apneas, Respiratory Effort Related Arousal (RERA), snoring, Cheyne-Stokes Respiration (CSR), respiratory insufficiency, Obesity Hyperventilation Syndrome (OHS), Chronic Obstructive Pulmonary Disease (COPD), Periodic Limb Movement Disorder (PLMD), Restless Leg Syndrome (RLS), Neuromuscular Disease (NMD), and chest wall disorders.

Obstructive Sleep Apnea (OSA), a form of Sleep Disordered Breathing (SDB), is characterized by events including occlusion or obstruction of the upper air passage during sleep resulting from a combination of an abnormally small upper airway and the normal loss of muscle tone in the region of the tongue, soft palate and posterior oropharyngeal wall. More generally, an apnea generally refers to the cessation of breathing caused by blockage of the air (Obstructive Sleep Apnea) or the stopping of the breathing function (often referred to as Central Sleep Apnea). CSA results when the brain temporarily stops sending signals to the muscles that control breathing. Typically, the individual will stop breathing for between about 15 seconds and about 30 seconds during an obstructive sleep apnea event.

Other types of apneas include hypopnea, hyperpnea, and hypercapnia. Hypopnea is generally characterized by slow or shallow breathing caused by a narrowed airway, as opposed to a blocked airway. Hyperpnea is generally characterized by an increase depth and/or rate of breathing. Hypercapnia is generally characterized by elevated or excessive carbon dioxide in the bloodstream, typically caused by inadequate respiration.

A Respiratory Effort Related Arousal (RERA) event is typically characterized by an increased respiratory effort for ten seconds or longer leading to arousal from sleep and which does not fulfill the criteria for an apnea or hypopnea event. RERAs are defined as a sequence of breaths characterized by increasing respiratory effort leading to an arousal from sleep, but which does not meet criteria for an apnea or hypopnea. These events fulfil the following criteria: (1) a pattern of progressively more negative esophageal pressure, terminated by a sudden change in pressure to a less negative level and an arousal, and (2) the event lasts ten seconds or longer. In some implementations, a Nasal Cannula/Pressure Transducer System is adequate and reliable in the detection of RERAs. A RERA detector may be based on a real flow signal derived from a respiratory therapy device. For example, a flow limitation measure may be determined based on a flow signal. A measure of arousal may then be derived as a function of the flow limitation measure and a measure of sudden increase in ventilation. One such method is described in WO 2008/138040 and U.S. Pat. No. 9,358, 353, assigned to ResMed Ltd., the disclosure of each of which is hereby incorporated by reference herein in their entireties.

Cheyne-Stokes Respiration (CSR) is another form of sleep disordered breathing. CSR is a disorder of a patient's respiratory controller in which there are rhythmic alternating periods of waxing and waning ventilation known as CSR cycles. CSR is characterized by repetitive de-oxygenation and re-oxygenation of the arterial blood.

Obesity Hyperventilation Syndrome (OHS) is defined as the combination of severe obesity and awake chronic hypercapnia, in the absence of other known causes for hypoventilation. Symptoms include dyspnea, morning headache and excessive daytime sleepiness.

Chronic Obstructive Pulmonary Disease (COPD) encompasses any of a group of lower airway diseases that have certain characteristics in common, such as increased resistance to air movement, extended expiratory phase of respiration, and loss of the normal elasticity of the lung. COPD encompasses a group of lower airway diseases that have certain characteristics in common, such as increased resistance to air movement, extended expiratory phase of respiration, and loss of the normal elasticity of the lung.

Neuromuscular Disease (NMD) encompasses many diseases and ailments that impair the functioning of the muscles either directly via intrinsic muscle pathology, or indirectly via nerve pathology. Chest wall disorders are a group of thoracic deformities that result in inefficient coupling between the respiratory muscles and the thoracic cage.

These and other disorders are characterized by particular events (e.g., snoring, an apnea, a hypopnea, a restless leg, a sleeping disorder, choking, an increased heart rate, labored breathing, an asthma attack, an epileptic episode, a seizure, or any combination thereof) that occur when the individual is sleeping.

The Apnea-Hypopnea Index (AHI) is an index used to indicate the severity of sleep apnea during a sleep session. The AHI is calculated by dividing the number of apnea and/or hypopnea events experienced by the user during the sleep session by the total number of hours of sleep in the sleep session. The event can be, for example, a pause in breathing that lasts for at least 10 seconds. An AHI that is less than 5 is considered normal. An AHI that is greater than or equal to 5, but less than 15 is considered indicative of mild sleep apnea. An AHI that is greater than or equal to 15, but less than 30 is considered indicative of moderate sleep apnea. An AHI that is greater than or equal to 30 is considered indicative of severe sleep apnea. In children, an AHI that is greater than 1 is considered abnormal. Sleep apnea can be considered "controlled" when the AHI is normal, or when the AHI is normal or mild. The AHI can also be used in combination with oxygen desaturation levels to indicate the severity of Obstructive Sleep Apnea.

Referring to FIG. 1, a system 10, according to some implementations of the present disclosure, is illustrated. The system 10 includes a respiratory therapy system 100, a control system 200, one or more sensors 210, a user device 260, and an activity tracker 270.

The respiratory therapy system 100 includes a respiratory pressure therapy (RPT) device 110 (referred to herein as respiratory therapy device 110), a user interface 120 (also referred to as a mask or a patient interface), a conduit 140 (also referred to as a tube or an air circuit), a display device 150, and a humidifier 160. Respiratory pressure therapy refers to the application of a supply of air to an entrance to a user's airways at a controlled target pressure that is nominally positive with respect to atmosphere throughout the user's breathing cycle (e.g., in contrast to negative pressure therapies such as the tank ventilator or cuirass). The respiratory therapy system 100 is generally used to treat individuals suffering from one or more sleep-related respiratory disorders (e.g., obstructive sleep apnea, central sleep apnea, or mixed sleep apnea).

The respiratory therapy system 100 can be used, for example, as a ventilator or as a positive airway pressure (PAP) system, such as a continuous positive airway pressure (CPAP) system, an automatic positive airway pressure system (APAP), a bi-level or variable positive airway pressure system (BPAP or VPAP), or any combination thereof. The CPAP system delivers a predetermined air pressure (e.g., determined by a sleep physician) to the user. The APAP system automatically varies the air pressure delivered to the user based on, for example, respiration data associated with the user. The BPAP or VPAP system is configured to deliver a first predetermined pressure (e.g., an inspiratory positive airway pressure or IPAP) and a second predetermined pressure (e.g., an expiratory positive airway pressure or EPAP) that is lower than the first predetermined pressure.

Figure 2:
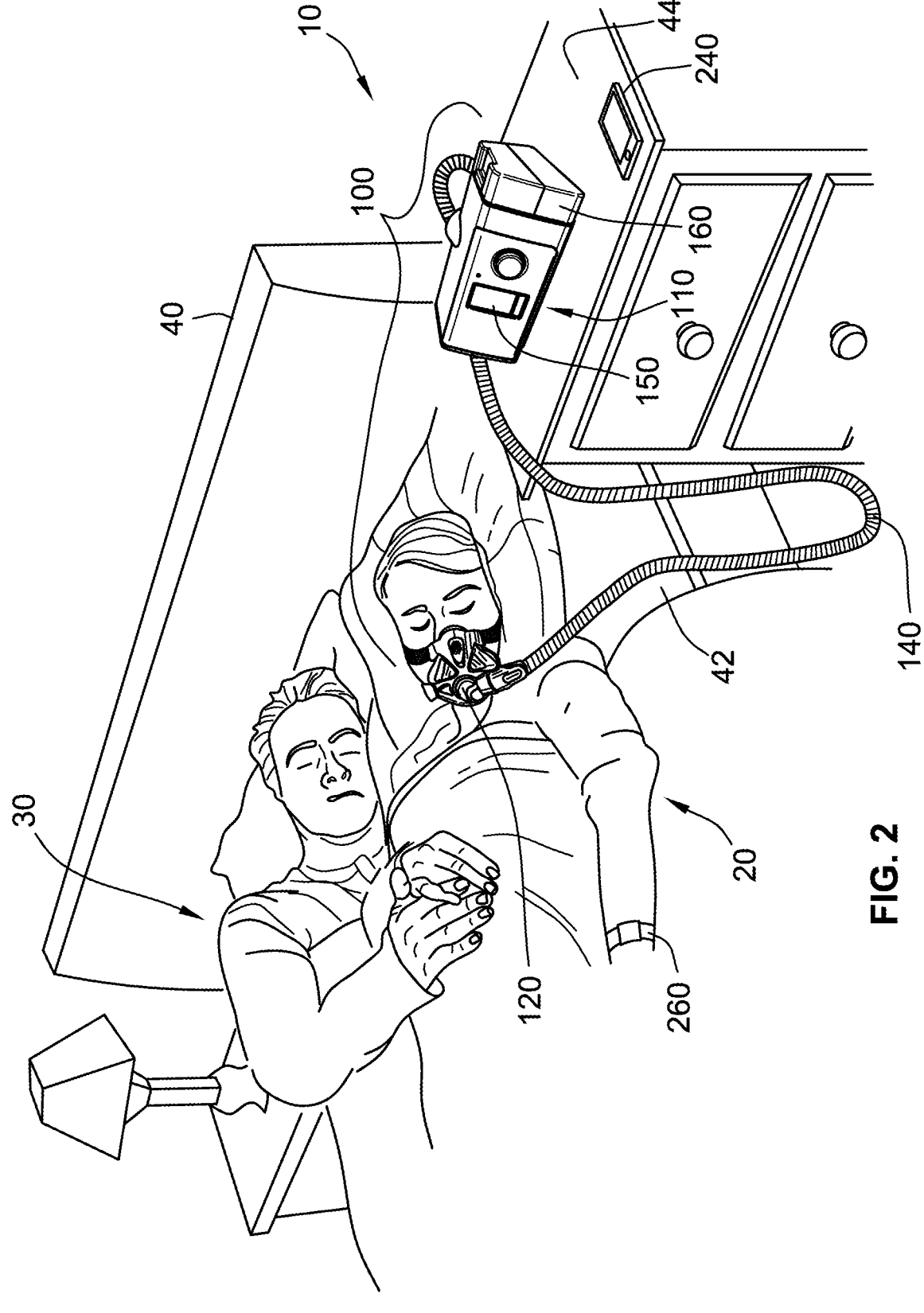
FIG. 2 is a perspective view of at least a portion of the system of FIG. 1, a user, and a bed partner, according to some implementations of the present disclosure.

As shown in FIG. 2, the respiratory therapy system 100 can be used to treat user 20. In this example, the user 20 of the respiratory therapy system 100 and a bed partner 30 are located in a bed 40 and are laying on a mattress 42. The user interface 120 can be worn by the user 20 during a sleep session. The respiratory therapy system 100 generally aids in increasing the air pressure in the throat of the user 20 to aid in preventing the airway from closing and/or narrowing during sleep. The respiratory therapy device 110 can be positioned on a nightstand 44 that is directly adjacent to the bed 40 as shown in FIG. 2, or more generally, on any surface or structure that is generally adjacent to the bed 40 and/or the user 20.

The respiratory therapy device 110 is generally used to generate pressurized air that is delivered to a user (e.g., using one or more motors that drive one or more compressors). In some implementations, the respiratory therapy device 110 generates continuous constant air pressure that is delivered to the user. In other implementations, the respiratory therapy device 110 generates two or more predetermined pressures (e.g., a first predetermined air pressure and a second predetermined air pressure). In still other implementations, the respiratory therapy device 110 generates a variety of different air pressures within a predetermined range. For example, the respiratory therapy device 110 can deliver at least about 6 cmH$_2$O, at least about 10 cmH$_2$O, at least about 20 cmH$_2$O, between about 6 cmH$_2$O and about 10 cmH$_2$O, between about 7 cmH$_2$O and about 12 cmH$_2$O, etc. The respiratory therapy device 110 can also deliver pressurized air at a predetermined flow rate between, for example, about −20 L/min and about 150 L/min, while maintaining a positive pressure (relative to the ambient pressure).

Figures 3A, 3B:
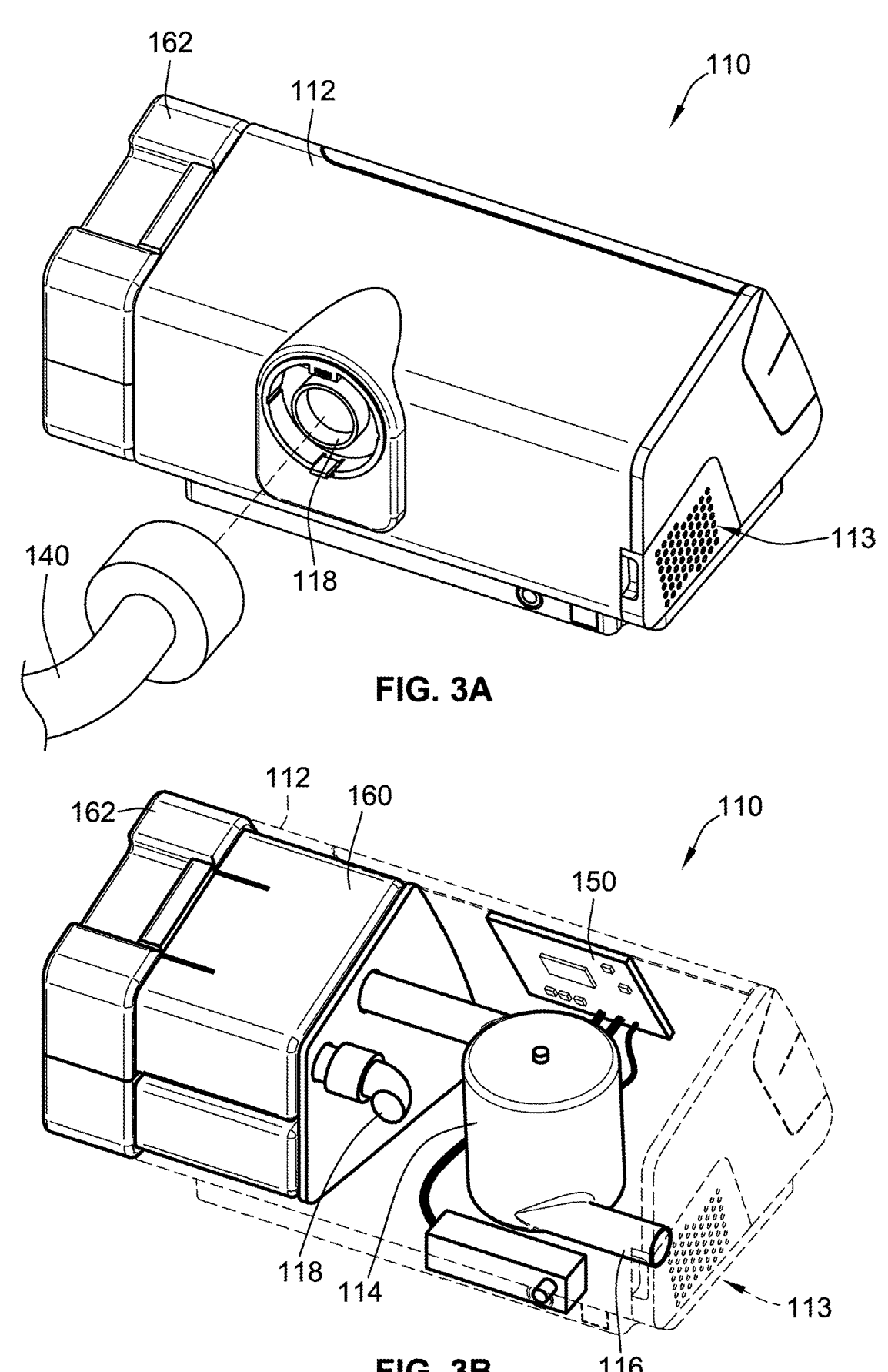
FIG. 3A is a perspective view of a respiratory therapy device of the system of FIG. 1, according to some implementations of the present disclosure.
FIG. 3B is a perspective view of the respiratory therapy device of FIG. 3A illustrating an interior of a housing, according to some implementations of the present disclosure.

The respiratory therapy device 110 includes a housing 112, a blower motor 114, an air inlet 116, and an air outlet 118 (FIG. 1). Referring to FIGS. 3A and 3B, the blower motor 114 is at least partially disposed or integrated within the housing 112. The blower motor 114 draws air from outside the housing 112 (e.g., atmosphere) via the air inlet 116 and causes pressurized air to flow through the humidifier 160, and through the air outlet 118. In some implementations, the air inlet 116 and/or the air outlet 118 include a cover that is moveable between a closed position and an open position (e.g., to prevent or inhibit air from flowing through the air inlet 116 or the air outlet 118). As shown in FIGS. 3A and 3B, the housing 112 can include a vent 113 to allow air to pass through the housing 112 to the air inlet 116. As described below, the conduit 140 is coupled to the air outlet 118 of the respiratory therapy device 110.

Referring back to FIG. 1, the user interface 120 engages a portion of the user's face and delivers pressurized air from the respiratory therapy device 110 to the user's airway to aid in preventing the airway from narrowing and/or collapsing during sleep. This may also increase the user's oxygen intake during sleep. Generally, the user interface 120 engages the user's face such that the pressurized air is delivered to the user's airway via the user's mouth, the user's nose, or both the user's mouth and nose. Together, the respiratory therapy device 110, the user interface 120, and the conduit 140 form an air pathway fluidly coupled with an airway of the user. The pressurized air also increases the user's oxygen intake during sleep. Depending upon the therapy to be applied, the user interface 120 may form a seal, for example, with a region or portion of the user's face, to facilitate the delivery of gas at a pressure at sufficient variance with ambient pressure to effect therapy, for example, at a positive pressure of about 10 cm H$_2$O relative to ambient pressure. For other forms of therapy, such as the delivery of oxygen, the user interface may not include a seal sufficient to facilitate delivery to the airways of a supply of gas at a positive pressure of about 10 cmH$_2$O.

The user interface 120 can include, for example, a cushion 122, a frame 124, a headgear 126, connector 128, and one or more vents 130. The cushion 122 and the frame 124 define a volume of space around the mouth and/or nose of the user. When the respiratory therapy system 100 is in use, this volume space receives pressurized air (e.g., from the respiratory therapy device 110 via the conduit 140) for passage into the airway(s) of the user. The headgear 126 is generally used to aid in positioning and/or stabilizing the user interface 120 on a portion of the user (e.g., the face), and along with the cushion 122 (which, for example, can comprise silicone, plastic, foam, etc.) aids in providing a substantially air-tight seal between the user interface 120 and the user 20. In some implementations the headgear 126 includes one or more straps (e.g., including hook and loop fasteners). The connector 128 is generally used to couple (e.g., connect and fluidly couple) the conduit 140 to the cushion 122 and/or frame 124. Alternatively, the conduit 140 can be directly coupled to the cushion 122 and/or frame 124 without the connector 128. The vent 130 can be used for permitting the escape of carbon dioxide and other gases exhaled by the user 20. The user interface 120 generally can include any suitable number of vents (e.g., one, two, five, ten, etc.).

As shown in FIG. 2, in some implementations, the user interface 120 is a facial mask (e.g., a full face mask) that covers at least a portion of the nose and mouth of the user 20. Alternatively, the user interface 120 can be a nasal mask that provides air to the nose of the user or a nasal pillow mask that delivers air directly to the nostrils of the user 20. In other implementations, the user interface 120 includes a mouthpiece (e.g., a night guard mouthpiece molded to conform to the teeth of the user, a mandibular repositioning device, etc.).

Figure 4A:
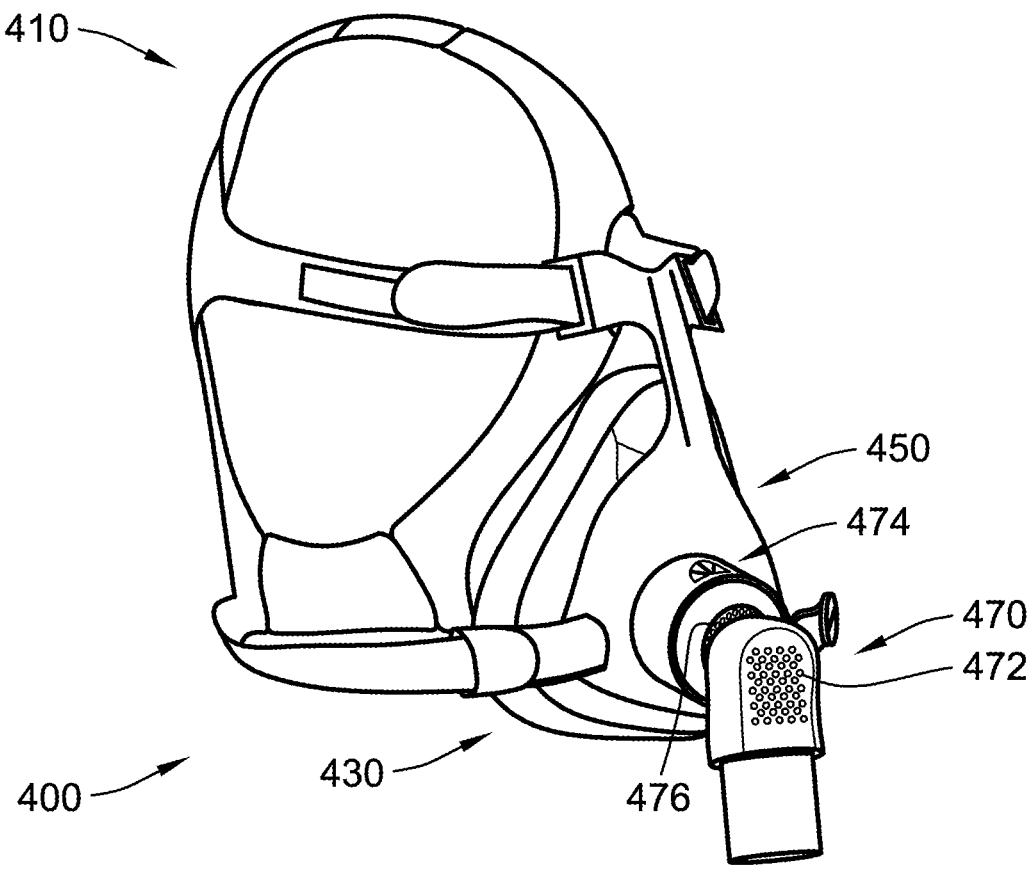
FIG. 4A is a perspective view of a user interface, according to some implementations of the present disclosure.
Figure 4B:
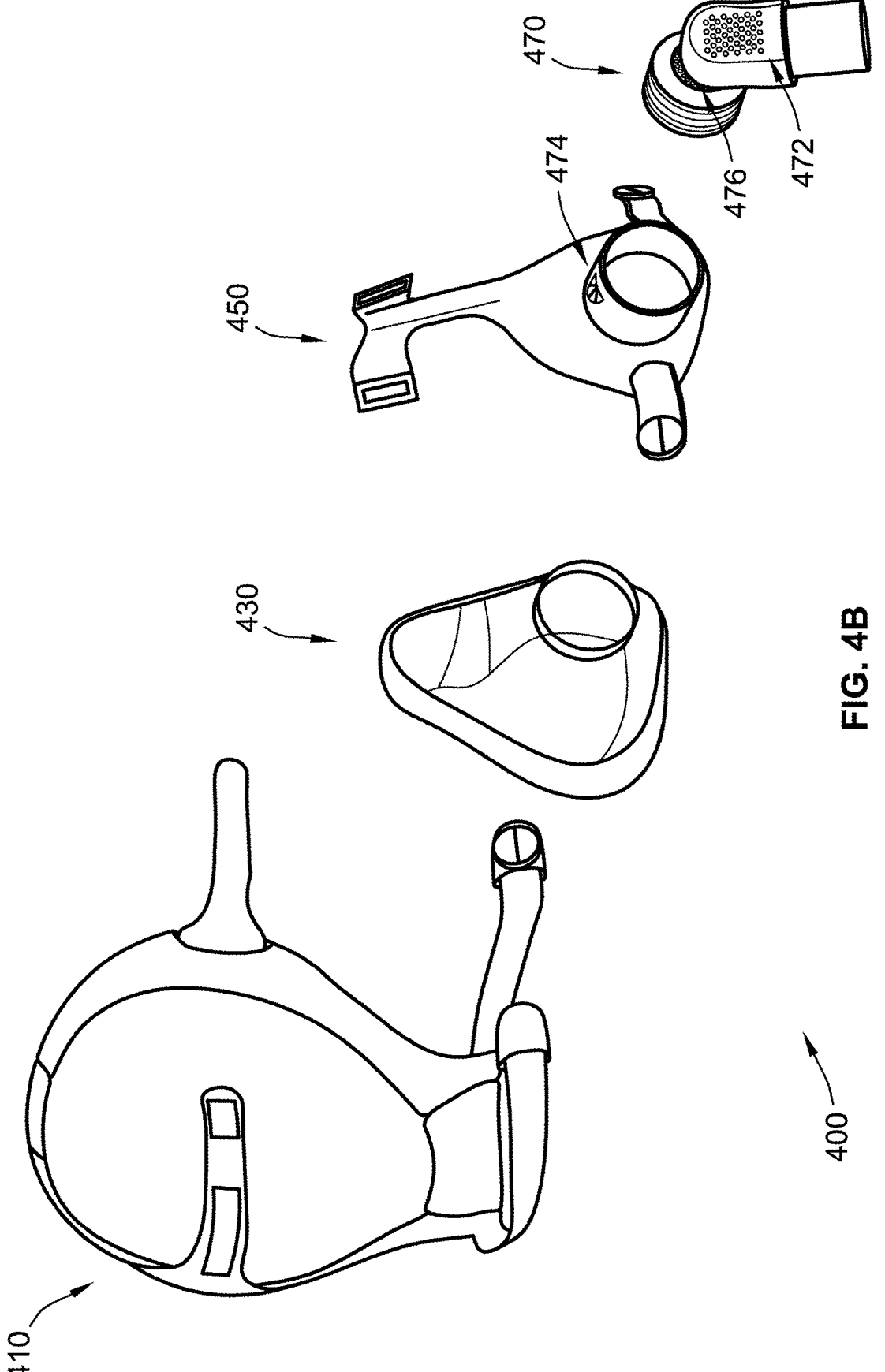
FIG. 4B is an exploded view of the user interface of FIG. 4A, according to some implementations of the present disclosure.

Referring to FIGS. 4A and 4B, a user interface 400 that is the same as, or similar to, the user interface 120 (FIG. 1) according to some implementations of the present disclosure is illustrated. The user interface 400 generally includes a cushion 430 and a frame 450 that define a volume of space around the mouth and/or nose of the user. When in use, the volume of space receives pressurized air for passage into the user's airways. In some implementations, the cushion 430 and frame 450 of the user interface 400 form a unitary component of the user interface. The user interface 400 can also include a headgear 410, which generally includes a strap assembly and optionally a connector 470. The headgear 410 is configured to be positioned generally about at least a portion of a user's head when the user wears the user interface 400. The headgear 410 can be coupled to the frame 450 and positioned on the user's head such that the user's head is positioned between the headgear 410 and the frame 450. The cushion 430 is positioned between the user's face and the frame 450 to form a seal on the user's face. The optional connector 470 is configured to couple to the frame 450 and/or cushion 430 at one end and to a conduit of a respiratory therapy device (not shown). The pressurized air can flow directly from the conduit of the respiratory therapy system into the volume of space defined by the cushion 430 (or cushion 430 and frame 450) of the user interface 400 through the connector 470). From the user interface 400, the pressurized air reaches the user's airway through the user's mouth, nose, or both. Alternatively, where the user interface 400 does not include the connector 470, the conduit of the respiratory therapy system can connect directly to the cushion 430 and/or the frame 450.

In some implementations, the connector 470 may include one or more vents 472 (e.g., a plurality of vents) located on the main body of the connector 470 itself and/or one or a plurality of vents 476 ("diffuser vents") in proximity to the frame 450, for permitting the escape of carbon dioxide (CO$_2$) and other gases exhaled by the user. In some implementations, one or a plurality of vents, such as vents 472 and/or 476 may be located in the user interface 400, such as in frame 450, and/or in the conduit 140. In some implementations, the frame 450 includes at least one anti-asphyxia valve (AAV) 474, which allows $CO_2$ and other gases exhaled by the user to escape in the event that the vents (e.g., the vents 472 or 476) fail when the respiratory therapy device is active. In general, AAVs (e.g., the AAV 474) are present for full face masks (e.g., as a safety feature); however, the diffuser vents and vents located on the mask or connector (usually an array of orifices in the mask material itself or a mesh made of some sort of fabric, in many cases replaceable) are not necessarily both present (e.g., some masks might have only the diffuser vents such as the plurality of vents 476, other masks might have only the plurality of vents 472 on the connector itself).

Figure 5A:
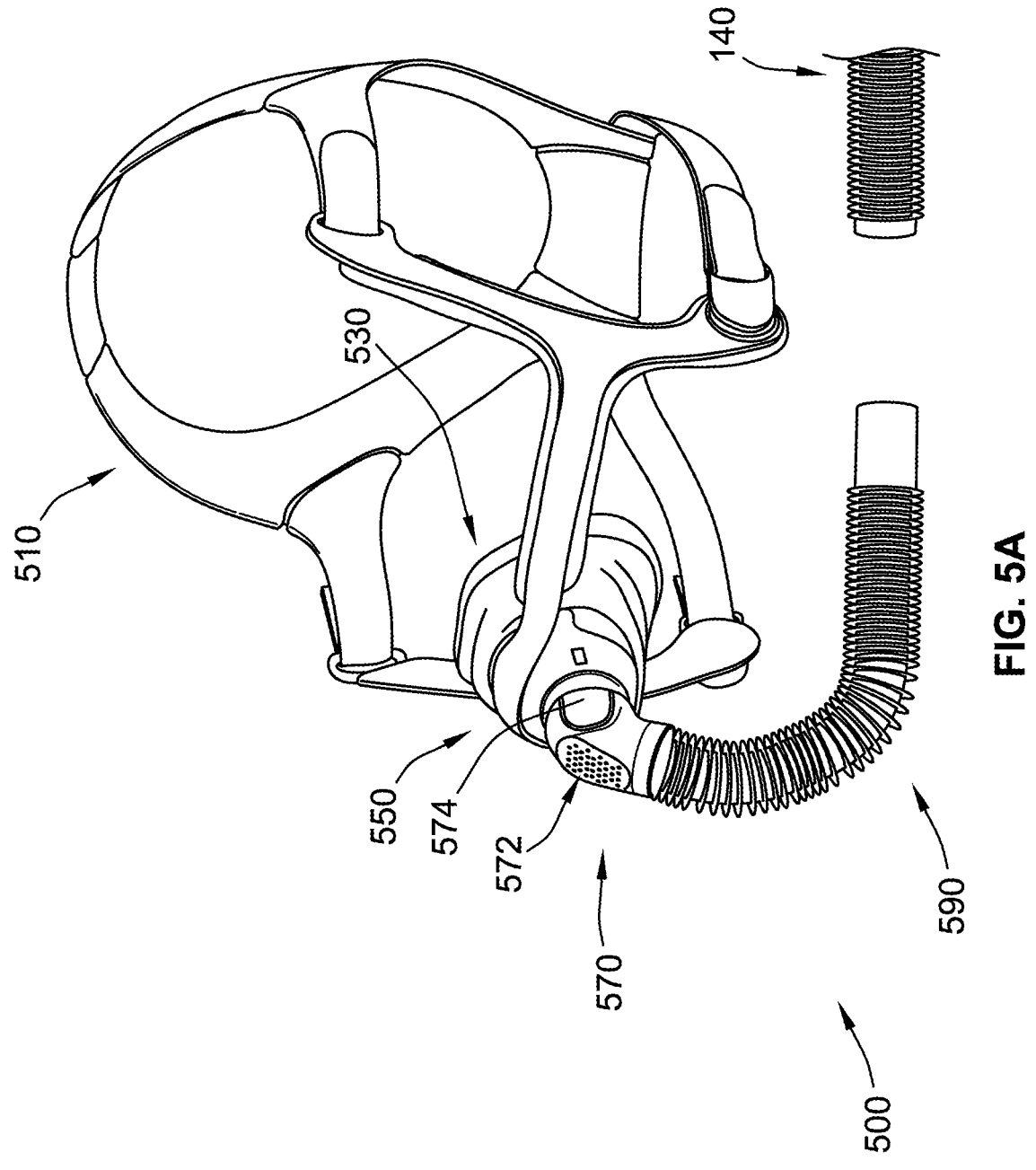
FIG. 5A is a perspective view of a user interface, according to some implementations of the present disclosure.
Figure 5B:
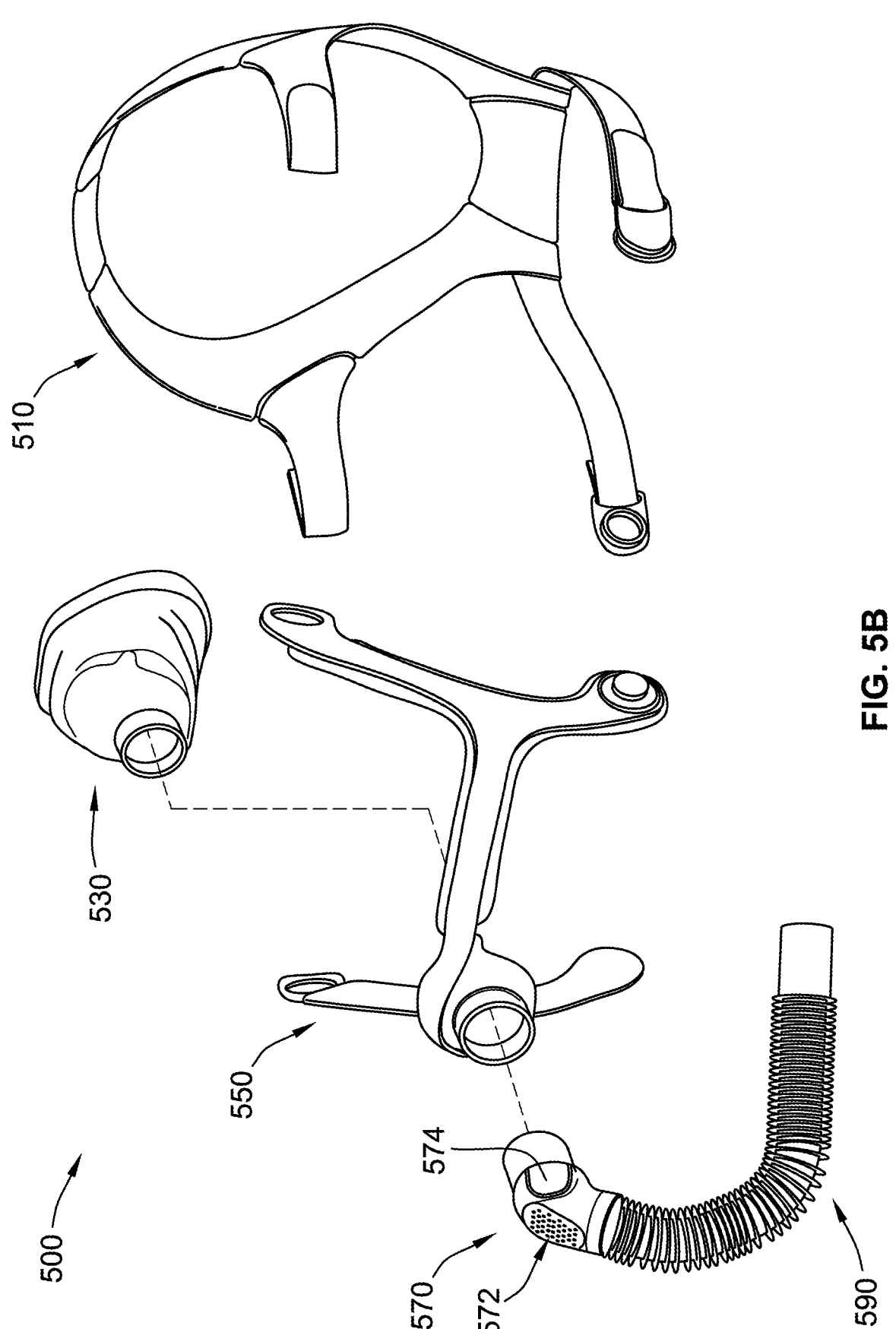
FIG. 5B is an exploded view of the user interface of FIG. 5A, according to some implementations of the present disclosure.

Referring to FIGS. 5A and 5B, a user interface 500 that the is the same, or similar to, the user interface 120 (FIG. 1) according to some implementations of the present disclosure is illustrated. The user interface 500 differs from the user interface 400 (FIGS. 4A and 4B) in that the user interface 500 is an indirect user interface, whereas the user interface 400 is a direct user interface. The interface 500 includes a headgear 510 (e.g., as a strap assembly), a cushion 530, a frame 550, a connector 570, and a user interface conduit 590 (often referred to as a minitube or a flexitube). The user interface 500 is an indirectly connected user interface because pressurized air is delivered from the conduit 140 of the respiratory therapy system to the cushion 530 and/or frame 550 through the user interface conduit 590, rather than directly from the conduit 140 of the respiratory therapy system.

In some implementations, the cushion 530 and frame 550 form a unitary component of the user interface 500. Generally, the user interface conduit 590 is more flexible than the conduit 140 of the respiratory therapy system 100 (FIG. 1) described above and/or has a diameter smaller than the diameter of the than the than the conduit 140. The user interface conduit 590 is typically shorter that conduit 140. Similar to the headgear 310 of user interface 300 (FIGS. 3A-3B), the headgear 510 of user interface 500 is configured to be positioned generally about at least a portion of a user's head when the user wears the user interface 500. The headgear 510 can be coupled to the frame 550 and positioned on the user's head such that the user's head is positioned between the headgear 510 and the frame 550. The cushion 530 is positioned between the user's face and the frame 550 to form a seal on the user's face. The connector 570 is configured to couple to the frame 550 and/or cushion 530 at one end and to the conduit 590 of the user interface 500 at the other end. In other implementations, the conduit 590 may connect directly to frame 550 and/or cushion 530. The conduit 590, at the opposite end relative to the frame 550 and cushion 530, is configured to connect to the conduit 140. The pressurized air can flow from the conduit 140 of the respiratory therapy system, through the user interface conduit 590, and the connector 570, and into a volume of space define by the cushion 530 (or cushion 530 and frame 550) of the user interface 500 against a user's face. From the volume of space, the pressurized air reaches the user's airway through the user's mouth, nose, or both.

In some implementations, the connector 570 includes a plurality of vents 572 for permitting the escape of carbon dioxide ($CO_2$) and other gases exhaled by the user when the respiratory therapy device is active. In such implementations, each of the plurality of vents 572 is an opening that may be angled relative to the thickness of the connector wall through which the opening is formed. The angled openings can reduce noise of the $CO_2$ and other gases escaping to the atmosphere. Because of the reduced noise, acoustic signal associated with the plurality of vents 572 may be more apparent to an internal microphone, as opposed to an external microphone. Thus, an internal microphone may be located within, or otherwise physically integrated with, the respiratory therapy system and in acoustic communication with the flow of air which, in operation, is generated by the flow generator of the respiratory therapy device, and passes through the conduit and to the user interface 500.

In some implementations, the connector 570 optionally includes at least one valve 574 for permitting the escape of $CO_2$ and other gases exhaled by the user when the respiratory therapy device is inactive. In some implementations, the valve 574 (an example of an anti-asphyxia valve) includes a silicone (or other suitable material) flap that is a failsafe component, which allows $CO_2$ and other gases exhaled by the user to escape in the event that the vents 572 fail when the respiratory therapy device is active. In such implementations, when the silicone flap is open, the valve opening is much greater than each vent opening, and therefore less likely to be blocked by occlusion materials.

Figure 6A:
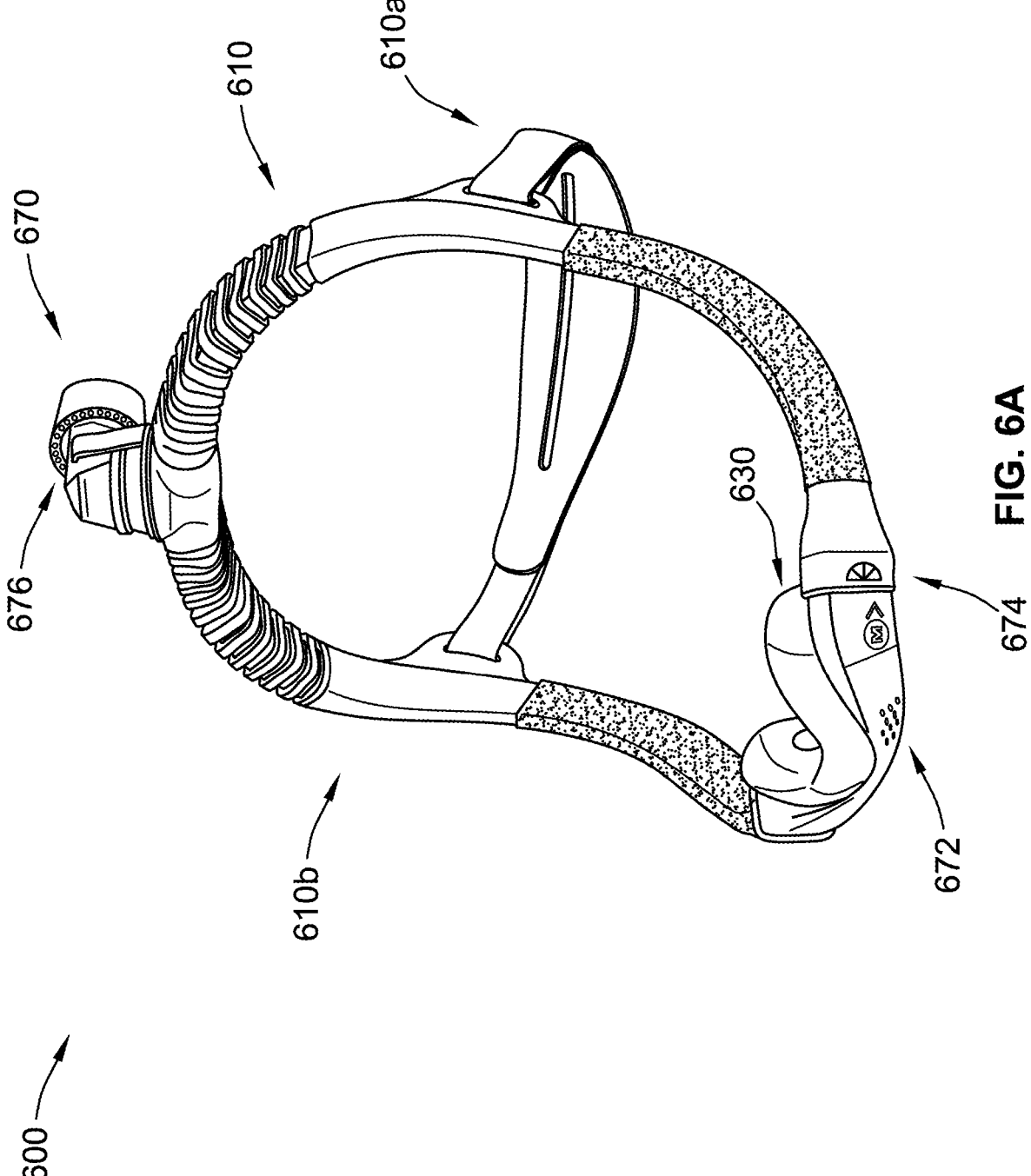
FIG. 6A is a perspective view of a user interface, according to some implementations of the present disclosure.
Figure 6B:
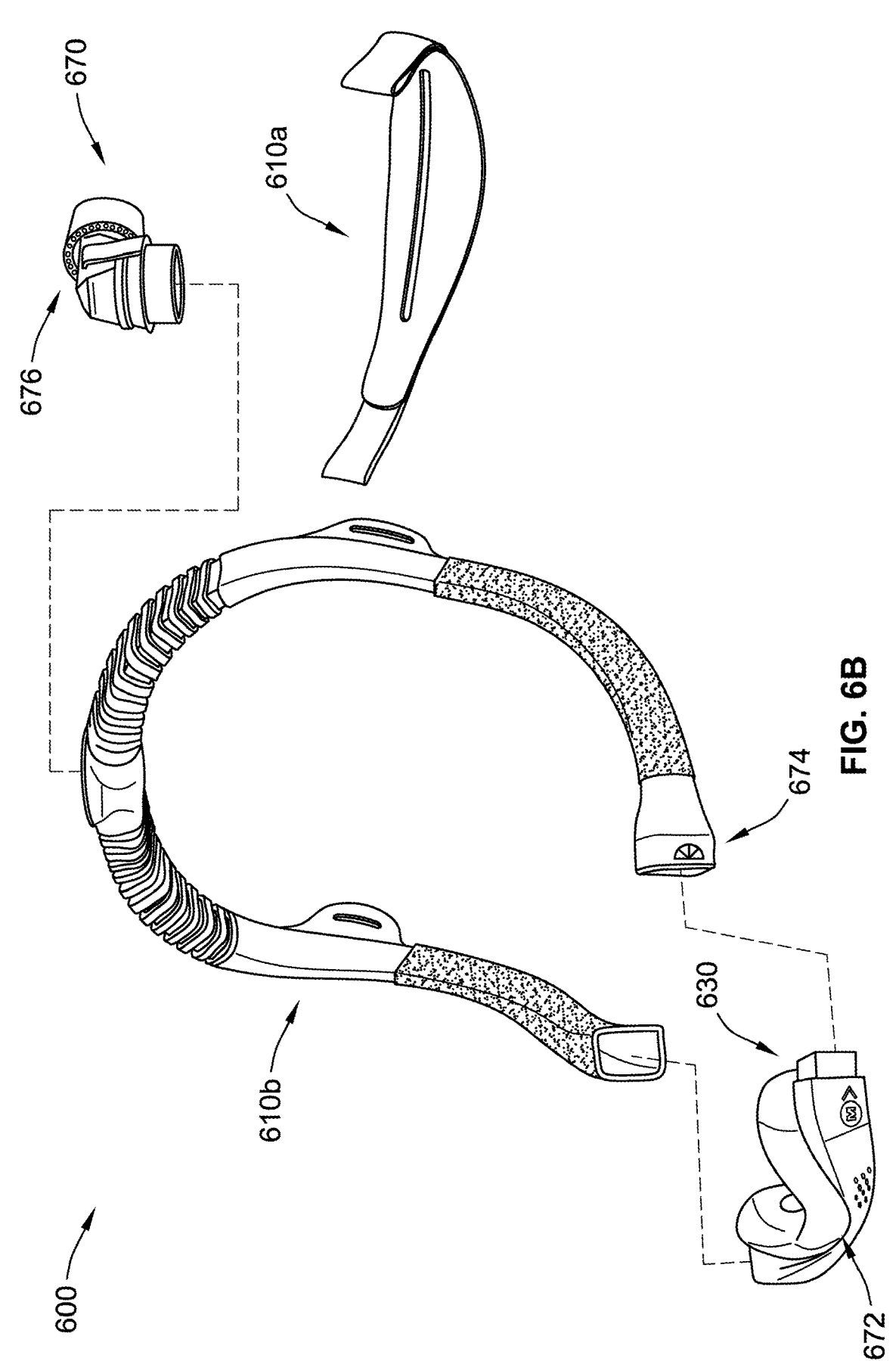
FIG. 6B is an exploded view of the user interface of FIG. 6A, according to some implementations of the present disclosure.

Referring to FIGS. 6A and 6B, a user interface 600 that is the same as, or similar to, the user interface 120 (FIG. 1) according to some implementations of the present disclosure is illustrated. The user interface 600 is similar to the user interface 500 in that it is an indirect user interface. The indirect headgear user interface 600 includes headgear 610, a cushion 630, and a connector 670. The headgear 610 includes strap 610*a* and a headgear conduit 610*b*. Similar to the user interface 400 (FIGS. 4A-4B) and user interface 500 (FIGS. 5A-5B), the headgear 610 is configured to be positioned generally about at least a portion of a user's head when the user wears the user interface 600. The headgear 610 includes a strap 610*a* that can be coupled to the headgear conduit 610*b* and positioned on the user's head such that the user's head is positioned between the strap 610*a* and the headgear conduit 610*b*. The cushion 630 is positioned between the user's face and the headgear conduit 610*b* to form a seal on the user's face.

The connector 670 is configured to couple to the headgear 610 at one end and a conduit of the respiratory therapy system at the other end (e.g., conduit 140). In other implementations, the connector 670 is not included and the headgear 610 can alternatively connect directly to conduit of the respiratory therapy system. The headgear conduit 610*b* can be configured to deliver pressurized air from the conduit of the respiratory therapy system to the cushion 630, or more specifically, to the volume of space around the mouth and/or nose of the user and enclosed by the user cushion. The headgear conduit 610*b* is hollow to provide a passageway for the pressurized air. Both sides of the headgear conduit 610*b* can be hollow to provide two passageways for the pressurized air. Alternatively, only one side of the headgear conduit 610*b* can be hollow to provide a single passageway. In the implementation illustrated in FIGS. 6A and 6B, headgear conduit 610*b* comprises two passageways which, in use, are positioned at either side of a user's head/face. Alternatively, only one passageway of the headgear conduit 610*b* can be hollow to provide a single passageway. The pressurized air can flow from the conduit of the respiratory therapy system, through the connector 670 and the headgear conduit 610*b*, and into the volume of space between the cushion 630 and the user's face. From the volume of space between the cushion 630 and the user's face, the pressurized air reaches the user's airway through the user's mouth, nose, or both.

In some implementations, the cushion 630 includes a plurality of vents 672 on the cushion 630 itself. Additionally or alternatively, in some implementations, the connector 670 includes a plurality of vents 676 ("diffuser vents") in proximity to the headgear 610, for permitting the escape of carbon dioxide ($CO_2$) and other gases exhaled by the user when the respiratory therapy device is active. In some implementations, the headgear 610 may include at least one plus anti-asphyxia valve (AAV) 674 in proximity to the cushion 630, which allows $CO_2$ and other gases exhaled by the user to escape in the event that the vents (e.g., the vents 672 or 676) fail when the respiratory therapy device is active.

Referring back to FIG. 1, the conduit 140 (also referred to as an air circuit or tube) allows the flow of air between components of the respiratory therapy system 100, such as between the respiratory therapy device 110 and the user interface 120. In some implementations, there can be separate limbs of the conduit for inhalation and exhalation. In other implementations, a single limb conduit is used for both inhalation and exhalation.

Referring to FIG. 3A, the conduit 140 includes a first end 142 that is coupled to the air outlet 118 of the respiratory therapy device 110. The first end 142 can be coupled to the air outlet 118 of the respiratory therapy device 110 using a variety of techniques (e.g., a press fit connection, a snap fit connection, a threaded connection, etc.). In some implementations, the conduit 140 includes one or more heating elements that heat the pressurized air flowing through the conduit 140 (e.g., heat the air to a predetermined temperature or within a range of predetermined temperatures). Such heating elements can be coupled to and/or imbedded in the conduit 140. In such implementations, the first end 142 can include an electrical contact that is electrically coupled to the respiratory therapy device 110 to power the one or more heating elements of the conduit 140. For example, the electrical contact can be electrically coupled to an electrical contact of the air outlet 118 of the respiratory therapy device 110. In this example, electrical contact of the conduit 140 can be a male connector and the electrical contact of the air outlet 118 can be female connector, or, alternatively, the opposite configuration can be used.

The display device 150 is generally used to display image(s) including still images, video images, or both and/or information regarding the respiratory therapy device 110. For example, the display device 150 can provide information regarding the status of the respiratory therapy device 110 (e.g., whether the respiratory therapy device 110 is on/off, the pressure of the air being delivered by the respiratory therapy device 110, the temperature of the air being delivered by the respiratory therapy device 110, etc.) and/or other information (e.g., a sleep score and/or a therapy score, also referred to as a myAir™ score, such as described in WO 2016/061629 and U.S. Patent Pub. No. 2017/0311879, which are hereby incorporated by reference herein in their entireties, the current date/time, personal information for the user 20, etc.). In some implementations, the display device 150 acts as a human-machine interface (HMI) that includes a graphic user interface (GUI) configured to display the image(s) as an input interface. The display device 150 can be an LED display, an OLED display, an LCD display, or the like. The input interface can be, for example, a touchscreen or touch-sensitive substrate, a mouse, a keyboard, or any sensor system configured to sense inputs made by a human user interacting with the respiratory therapy device 110.

The humidifier 160 is coupled to or integrated in the respiratory therapy device 110 and includes a reservoir 162 for storing water that can be used to humidify the pressurized air delivered from the respiratory therapy device 110. The humidifier 160 includes a one or more heating elements

164 to heat the water in the reservoir to generate water vapor. The humidifier 160 can be fluidly coupled to a water vapor inlet of the air pathway between the blower motor 114 and the air outlet 118, or can be formed in-line with the air pathway between the blower motor 114 and the air outlet 118. For example, as shown in FIG. 3, air flow from the air inlet 116 through the blower motor 114, and then through the humidifier 160 before exiting the respiratory therapy device 110 via the air outlet 118.

While the respiratory therapy system 100 has been described herein as including each of the respiratory therapy device 110, the user interface 120, the conduit 140, the display device 150, and the humidifier 160, more or fewer components can be included in a respiratory therapy system according to implementations of the present disclosure. For example, a first alternative respiratory therapy system includes the respiratory therapy device 110, the user interface 120, and the conduit 140. As another example, a second alternative system includes the respiratory therapy device 110, the user interface 120, and the conduit 140, and the display device 150. Thus, various respiratory therapy systems can be formed using any portion or portions of the components shown and described herein and/or in combination with one or more other components.

The control system 200 includes one or more processors 202 (hereinafter, processor 202). The control system 200 is generally used to control (e.g., actuate) the various components of the system 10 and/or analyze data obtained and/or generated by the components of the system 10. The processor 202 can be a general or special purpose processor or microprocessor. While one processor 202 is illustrated in FIG. 1, the control system 200 can include any number of processors (e.g., one processor, two processors, five processors, ten processors, etc.) that can be in a single housing, or located remotely from each other. The control system 200 (or any other control system) or a portion of the control system 200 such as the processor 202 (or any other processor(s) or portion(s) of any other control system), can be used to carry out one or more steps of any of the methods described and/or claimed herein. The control system 200 can be coupled to and/or positioned within, for example, a housing of the user device 260, a portion (e.g., the respiratory therapy device 110) of the respiratory therapy system 100, and/or within a housing of one or more of the sensors 210. The control system 200 can be centralized (within one such housing) or decentralized (within two or more of such housings, which are physically distinct). In such implementations including two or more housings containing the control system 200, the housings can be located proximately and/or remotely from each other.

The memory device 204 stores machine-readable instructions that are executable by the processor 202 of the control system 200. The memory device 204 can be any suitable computer readable storage device or media, such as, for example, a random or serial access memory device, a hard drive, a solid state drive, a flash memory device, etc. While one memory device 204 is shown in FIG. 1, the system 10 can include any suitable number of memory devices 204 (e.g., one memory device, two memory devices, five memory devices, ten memory devices, etc.). The memory device 204 can be coupled to and/or positioned within a housing of a respiratory therapy device 110 of the respiratory therapy system 100, within a housing of the user device 260, within a housing of one or more of the sensors 210, or any combination thereof. Like the control system 200, the memory device 204 can be centralized (within one such housing) or decentralized (within two or more of such housings, which are physically distinct).

In some implementations, the memory device 204 stores a user profile associated with the user. The user profile can include, for example, demographic information associated with the user, biometric information associated with the user, medical information associated with the user, self-reported user feedback, sleep parameters associated with the user (e.g., sleep-related parameters recorded from one or more earlier sleep sessions), or any combination thereof. The demographic information can include, for example, information indicative of an age of the user, a gender of the user, a race of the user, a geographic location of the user, a relationship status, a family history of insomnia or sleep apnea, an employment status of the user, an educational status of the user, a socioeconomic status of the user, or any combination thereof. The medical information can include, for example, information indicative of one or more medical conditions associated with the user, medication usage by the user, or both. The medical information data can further include a multiple sleep latency test (MSLT) result or score and/or a Pittsburgh Sleep Quality Index (PSQI) score or value. The self-reported user feedback can include information indicative of a self-reported subjective sleep score (e.g., poor, average, excellent), a self-reported subjective stress level of the user, a self-reported subjective fatigue level of the user, a self-reported subjective health status of the user, a recent life event experienced by the user, or any combination thereof.

As described herein, the processor 202 and/or memory device 204 can receive data (e.g., physiological data and/or audio data) from the one or more sensors 210 such that the data for storage in the memory device 204 and/or for analysis by the processor 202. The processor 202 and/or memory device 204 can communicate with the one or more sensors 210 using a wired connection or a wireless connection (e.g., using an RF communication protocol, a Wi-Fi communication protocol, a Bluetooth communication protocol, over a cellular network, etc.). In some implementations, the system 10 can include an antenna, a receiver (e.g., an RF receiver), a transmitter (e.g., an RF transmitter), a transceiver, or any combination thereof. Such components can be coupled to or integrated a housing of the control system 200 (e.g., in the same housing as the processor 202 and/or memory device 204), or the user device 260.

Referring to back to FIG. 1, the one or more sensors 210 include a pressure sensor 212, a flow rate sensor 214, temperature sensor 216, a motion sensor 218, a microphone 220, a speaker 222, a radio-frequency (RF) receiver 226, a RF transmitter 228, a camera 232, an infrared sensor 234, a photoplethysmogram (PPG) sensor 236, an electrocardiogram (ECG) sensor 238, an electroencephalography (EEG) sensor 240, a capacitive sensor 242, a force sensor 244, a strain gauge sensor 246, an electromyography (EMG) sensor 248, an oxygen sensor 250, an analyte sensor 252, a moisture sensor 254, a LiDAR sensor 256, or any combination thereof. Generally, each of the one or more sensors 210 are configured to output sensor data that is received and stored in the memory device 204 or one or more other memory devices.

While the one or more sensors 210 are shown and described as including each of the pressure sensor 212, the flow rate sensor 214, the temperature sensor 216, the motion sensor 218, the microphone 220, the speaker 222, the RF receiver 226, the RF transmitter 228, the camera 232, the infrared sensor 234, the photoplethysmogram (PPG) sensor 236, the electrocardiogram (ECG) sensor 238, the electroencephalography (EEG) sensor 240, the capacitive sensor 242, the force sensor 244, the strain gauge sensor 246, the electromyography (EMG) sensor 248, the oxygen sensor 250, the analyte sensor 252, the moisture sensor 254, and the LiDAR sensor 256, more generally, the one or more sensors 210 can include any combination and any number of each of the sensors described and/or shown herein.

As described herein, the system 10 generally can be used to generate physiological data associated with a user (e.g., a user of the respiratory therapy system 100) during a sleep session. The physiological data can be analyzed to generate one or more sleep-related parameters, which can include any parameter, measurement, etc. related to the user during the sleep session. The one or more sleep-related parameters that can be determined for the user 20 during the sleep session include, for example, an Apnea-Hypopnea Index (AHI) score, a sleep score, a flow signal, a respiration signal, a respiration rate, an inspiration amplitude, an expiration amplitude, an inspiration-expiration ratio, a number of events per hour, a pattern of events, a stage, pressure settings of the respiratory therapy device 110, a heart rate, a heart rate variability, movement of the user 20, temperature, EEG activity, EMG activity, arousal, snoring, choking, coughing, whistling, wheezing, or any combination thereof.

The one or more sensors 210 can be used to generate, for example, physiological data, audio data, or both. Physiological data generated by one or more of the sensors 210 can be used by the control system 200 to determine a sleep-wake signal associated with the user 20 (FIG. 2) during the sleep session and one or more sleep-related parameters. The sleep-wake signal can be indicative of one or more sleep states, including wakefulness, relaxed wakefulness, micro-awakenings, or distinct sleep stages such as, for example, a rapid eye movement (REM) stage, a first non-REM stage (often referred to as "N1"), a second non-REM stage (often referred to as "N2"), a third non-REM stage (often referred to as "N3"), or any combination thereof. Methods for determining sleep states and/or sleep stages from physiological data generated by one or more sensors, such as the one or more sensors 210, are described in, for example, WO 2014/047310, U.S. Patent Pub. No. 2014/0088373, WO 2017/132726, WO 2019/122413, WO 2019/122414, and U.S. Patent Pub. No. 2020/0383580 each of which is hereby incorporated by reference herein in its entirety.

In some implementations, the sleep-wake signal described herein can be timestamped to indicate a time that the user enters the bed, a time that the user exits the bed, a time that the user attempts to fall asleep, etc. The sleep-wake signal can be measured by the one or more sensors 210 during the sleep session at a predetermined sampling rate, such as, for example, one sample per second, one sample per 30 seconds, one sample per minute, etc. In some implementations, the sleep-wake signal can also be indicative of a respiration signal, a respiration rate, an inspiration amplitude, an expiration amplitude, an inspiration-expiration ratio, a number of events per hour, a pattern of events, pressure settings of the respiratory therapy device 110, or any combination thereof during the sleep session. The event(s) can include snoring, apneas, central apneas, obstructive apneas, mixed apneas, hypopneas, a mask leak (e.g., from the user interface 120), a restless leg, a sleeping disorder, choking, an increased heart rate, labored breathing, an asthma attack, an epileptic episode, a seizure, or any combination thereof. The one or more sleep-related parameters that can be determined for the user during the sleep session based on the sleep-wake signal include, for example, a total time in bed, a total sleep time, a sleep onset latency, a wake-after-sleep-onset parameter, a sleep efficiency, a fragmentation index, or any combination thereof. As described in further detail herein, the physiological data and/or the sleep-related parameters can be analyzed to determine one or more sleep-related scores.

Physiological data and/or audio data generated by the one or more sensors 210 can also be used to determine a respiration signal associated with a user during a sleep session. The respiration signal is generally indicative of respiration or breathing of the user during the sleep session. The respiration signal can be indicative of and/or analyzed to determine (e.g., using the control system 200) one or more sleep-related parameters, such as, for example, a respiration rate, a respiration rate variability, an inspiration amplitude, an expiration amplitude, an inspiration-expiration ratio, an occurrence of one or more events, a number of events per hour, a pattern of events, a sleep state, a sleet stage, an apnea-hypopnea index (AHI), pressure settings of the respiratory therapy device 110, or any combination thereof. The one or more events can include snoring, apneas, central apneas, obstructive apneas, mixed apneas, hypopneas, a mask leak (e.g., from the user interface 120), a cough, a restless leg, a sleeping disorder, choking, an increased heart rate, labored breathing, an asthma attack, an epileptic episode, a seizure, increased blood pressure, or any combination thereof. Many of the described sleep-related parameters are physiological parameters, although some of the sleep-related parameters can be considered to be non-physiological parameters. Other types of physiological and/or non-physiological parameters can also be determined, either from the data from the one or more sensors 210, or from other types of data.

The pressure sensor 212 outputs pressure data that can be stored in the memory device 204 and/or analyzed by the processor 202 of the control system 200. In some implementations, the pressure sensor 212 is an air pressure sensor (e.g., barometric pressure sensor) that generates sensor data indicative of the respiration (e.g., inhaling and/or exhaling) of the user of the respiratory therapy system 100 and/or ambient pressure. In such implementations, the pressure sensor 212 can be coupled to or integrated in the respiratory therapy device 110. The pressure sensor 212 can be, for example, a capacitive sensor, an electromagnetic sensor, a piezoelectric sensor, a strain-gauge sensor, an optical sensor, a potentiometric sensor, or any combination thereof.

The flow rate sensor 214 outputs flow rate data that can be stored in the memory device 204 and/or analyzed by the processor 202 of the control system 200. Examples of flow rate sensors (such as, for example, the flow rate sensor 214) are described in International Publication No. WO 2012/012835 and U.S. Pat. No. 10,328,219, both of which are hereby incorporated by reference herein in their entireties. In some implementations, the flow rate sensor 214 is used to determine an air flow rate from the respiratory therapy device 110, an air flow rate through the conduit 140, an air flow rate through the user interface 120, or any combination thereof. In such implementations, the flow rate sensor 214 can be coupled to or integrated in the respiratory therapy device 110, the user interface 120, or the conduit 140. The flow rate sensor 214 can be a mass flow rate sensor such as, for example, a rotary flow meter (e.g., Hall effect flow meters), a turbine flow meter, an orifice flow meter, an ultrasonic flow meter, a hot wire sensor, a vortex sensor, a membrane sensor, or any combination thereof. In some implementations, the flow rate sensor 214 is configured to measure a vent flow (e.g., intentional "leak"), an unintentional leak (e.g., mouth leak and/or mask leak), a patient flow (e.g., air into and/or out of lungs), or any combination thereof. In some implementations, the flow rate data can be analyzed to determine cardiogenic oscillations of the user. In some examples, the pressure sensor 212 can be used to determine a blood pressure of a user.

The temperature sensor 216 outputs temperature data that can be stored in the memory device 204 and/or analyzed by the processor 202 of the control system 200. In some implementations, the temperature sensor 216 generates temperatures data indicative of a core body temperature of the user 20 (FIG. 2), a skin temperature of the user 20, a temperature of the air flowing from the respiratory therapy device 110 and/or through the conduit 140, a temperature in the user interface 120, an ambient temperature, or any combination thereof. The temperature sensor 216 can be, for example, a thermocouple sensor, a thermistor sensor, a silicon band gap temperature sensor or semiconductor-based sensor, a resistance temperature detector, or any combination thereof.

The motion sensor 218 outputs motion data that can be stored in the memory device 204 and/or analyzed by the processor 202 of the control system 200. The motion sensor 218 can be used to detect movement of the user 20 during the sleep session, and/or detect movement of any of the components of the respiratory therapy system 100, such as the respiratory therapy device 110, the user interface 120, or the conduit 140. The motion sensor 218 can include one or more inertial sensors, such as accelerometers, gyroscopes, and magnetometers. In some implementations, the motion sensor 218 alternatively or additionally generates one or more signals representing bodily movement of the user, from which may be obtained a signal representing a sleep state of the user; for example, via a respiratory movement of the user. In some implementations, the motion data from the motion sensor 218 can be used in conjunction with additional data from another one of the sensors 210 to determine the sleep state of the user.

The microphone 220 outputs sound and/or audio data that can be stored in the memory device 204 and/or analyzed by the processor 202 of the control system 200. The audio data generated by the microphone 220 is reproducible as one or more sound(s) during a sleep session (e.g., sounds from the user 20). The audio data form the microphone 220 can also be used to identify (e.g., using the control system 200) an event experienced by the user during the sleep session, as described in further detail herein. The microphone 220 can be coupled to or integrated in the respiratory therapy device 110, the user interface 120, the conduit 140, or the user device 260. In some implementations, the system 10 includes a plurality of microphones (e.g., two or more microphones and/or an array of microphones with beamforming) such that sound data generated by each of the plurality of microphones can be used to discriminate the sound data generated by another of the plurality of microphones The speaker 222 outputs sound waves that are audible to a user of the system 10 (e.g., the user 20 of FIG. 2). The speaker 222 can be used, for example, as an alarm clock or to play an alert or message to the user 20 (e.g., in response to an event). In some implementations, the speaker 222 can be used to communicate the audio data generated by the microphone 220 to the user. The speaker 222 can be coupled to or integrated in the respiratory therapy device 110, the user interface 120, the conduit 140, or the user device 260.

The microphone 220 and the speaker 222 can be used as separate devices. In some implementations, the microphone 220 and the speaker 222 can be combined into an acoustic sensor 224 (e.g., a SONAR sensor), as described in, for example, WO 2018/050913, WO 2020/104465, U.S. Pat. App. Pub. No. 2022/0007965, each of which is hereby incorporated by reference herein in its entirety. In such implementations, the speaker 222 generates or emits sound waves at a predetermined interval and the microphone 220 detects the reflections of the emitted sound waves from the speaker 222. The sound waves generated or emitted by the speaker 222 have a frequency that is not audible to the human ear (e.g., below 20 Hz or above around 18 kHz) so as not to disturb the sleep of the user 20 or the bed partner 30 (FIG. 2). Based at least in part on the data from the microphone 220 and/or the speaker 222, the control system 200 can determine a location of the user 20 (FIG. 2) and/or one or more of the sleep-related parameters described in herein such as, for example, a respiration signal, a respiration rate, an inspiration amplitude, an expiration amplitude, an inspiration-expiration ratio, a number of events per hour, a pattern of events, a sleep state, a sleep stage, pressure settings of the respiratory therapy device 110, or any combination thereof. In such a context, a sonar sensor may be understood to concern an active acoustic sensing, such as by generating and/or transmitting ultrasound and/or low frequency ultrasound sensing signals (e.g., in a frequency range of about 17-23 kHz, 18-22 kHz, or 17-18 kHz, for example), through the air.

In some implementations, the sensors 210 include (i) a first microphone that is the same as, or similar to, the microphone 220, and is integrated in the acoustic sensor 224 and (ii) a second microphone that is the same as, or similar to, the microphone 220, but is separate and distinct from the first microphone that is integrated in the acoustic sensor 224.

The RF transmitter 228 generates and/or emits radio waves having a predetermined frequency and/or a predetermined amplitude (e.g., within a high frequency band, within a low frequency band, long wave signals, short wave signals, etc.). The RF receiver 226 detects the reflections of the radio waves emitted from the RF transmitter 228, and this data can be analyzed by the control system 200 to determine a location of the user and/or one or more of the sleep-related parameters described herein. An RF receiver (either the RF receiver 226 and the RF transmitter 228 or another RF pair) can also be used for wireless communication between the control system 200, the respiratory therapy device 110, the one or more sensors 210, the user device 260, or any combination thereof. While the RF receiver 226 and RF transmitter 228 are shown as being separate and distinct elements in FIG. 1, in some implementations, the RF receiver 226 and RF transmitter 228 are combined as a part of an RF sensor 230 (e.g. a RADAR sensor). In some such implementations, the RF sensor 230 includes a control circuit. The format of the RF communication can be Wi-Fi, Bluetooth, or the like.

In some implementations, the RF sensor 230 is a part of a mesh system. One example of a mesh system is a Wi-Fi mesh system, which can include mesh nodes, mesh router(s), and mesh gateway(s), each of which can be mobile/movable or fixed. In such implementations, the Wi-Fi mesh system includes a Wi-Fi router and/or a Wi-Fi controller and one or more satellites (e.g., access points), each of which include an RF sensor that the is the same as, or similar to, the RF sensor 230. The Wi-Fi router and satellites continuously communicate with one another using Wi-Fi signals. The Wi-Fi mesh system can be used to generate motion data based on changes in the Wi-Fi signals (e.g., differences in received signal strength) between the router and the satellite(s) due to an object or person moving partially obstructing the signals. The motion data can be indicative of motion, breathing, heart rate, gait, falls, behavior, etc., or any combination thereof.

The camera 232 outputs image data reproducible as one or more images (e.g., still images, video images, thermal images, or any combination thereof) that can be stored in the memory device 204. The image data from the camera 232 can be used by the control system 200 to determine one or more of the sleep-related parameters described herein, such as, for example, one or more events (e.g., periodic limb movement or restless leg syndrome), a respiration signal, a respiration rate, an inspiration amplitude, an expiration amplitude, an inspiration-expiration ratio, a number of events per hour, a pattern of events, a sleep state, a sleep stage, or any combination thereof. Further, the image data from the camera 232 can be used to, for example, identify a location of the user, to determine chest movement of the user (FIG. 2), to determine air flow of the mouth and/or nose of the user, to determine a time when the user enters the bed (FIG. 2), and to determine a time when the user exits the bed. In some implementations, the camera 232 includes a wide angle lens or a fish eye lens.

The infrared (IR) sensor 234 outputs infrared image data reproducible as one or more infrared images (e.g., still images, video images, or both) that can be stored in the memory device 204. The infrared data from the IR sensor 234 can be used to determine one or more sleep-related parameters during a sleep session, including a temperature of the user 20 and/or movement of the user 20. The IR sensor 234 can also be used in conjunction with the camera 232 when measuring the presence, location, and/or movement of the user 20. The IR sensor 234 can detect infrared light having a wavelength between about 700 nm and about 1 mm, for example, while the camera 232 can detect visible light having a wavelength between about 380 nm and about 740 nm.

The PPG sensor 236 outputs physiological data associated with the user 20 (FIG. 2) that can be used to determine one or more sleep-related parameters, such as, for example, a heart rate, a heart rate variability, a cardiac cycle, respiration rate, an inspiration amplitude, an expiration amplitude, an inspiration-expiration ratio, estimated blood pressure parameter(s), or any combination thereof. The PPG sensor 236 can be worn by the user 20, embedded in clothing and/or fabric that is worn by the user 20, embedded in and/or coupled to the user interface 120 and/or its associated headgear (e.g., straps, etc.), etc.

The ECG sensor 238 outputs physiological data associated with electrical activity of the heart of the user 20. In some implementations, the ECG sensor 238 includes one or more electrodes that are positioned on or around a portion of the user 20 during the sleep session. The physiological data from the ECG sensor 238 can be used, for example, to determine one or more of the sleep-related parameters described herein.

The EEG sensor 240 outputs physiological data associated with electrical activity of the brain of the user 20. In some implementations, the EEG sensor 240 includes one or more electrodes that are positioned on or around the scalp of the user 20 during the sleep session. The physiological data from the EEG sensor 240 can be used, for example, to determine a sleep state and/or a sleep stage of the user 20 at any given time during the sleep session. In some implementations, the EEG sensor 240 can be integrated in the user interface 120 and/or the associated headgear (e.g., straps, etc.).

The capacitive sensor 242, the force sensor 244, and the strain gauge sensor 246 output data that can be stored in the memory device 204 and used/analyzed by the control system 200 to determine, for example, one or more of the sleep-related parameters described herein. The EMG sensor 248 outputs physiological data associated with electrical activity produced by one or more muscles. The oxygen sensor 250 outputs oxygen data indicative of an oxygen concentration of gas (e.g., in the conduit 140 or at the user interface 120). The oxygen sensor 250 can be, for example, an ultrasonic oxygen sensor, an electrical oxygen sensor, a chemical oxygen sensor, an optical oxygen sensor, a pulse oximeter (e.g., $SpO_2$ sensor), or any combination thereof.

The analyte sensor 252 can be used to detect the presence of an analyte in the exhaled breath of the user 20. The data output by the analyte sensor 252 can be stored in the memory device 204 and used by the control system 200 to determine the identity and concentration of any analytes in the breath of the user. In some implementations, the analyte sensor 174 is positioned near a mouth of the user to detect analytes in breath exhaled from the user's mouth. For example, when the user interface 120 is a facial mask that covers the nose and mouth of the user, the analyte sensor 252 can be positioned within the facial mask to monitor the user's mouth breathing. In other implementations, such as when the user interface 120 is a nasal mask or a nasal pillow mask, the analyte sensor 252 can be positioned near the nose of the user to detect analytes in breath exhaled through the user's nose. In still other implementations, the analyte sensor 252 can be positioned near the user's mouth when the user interface 120 is a nasal mask or a nasal pillow mask. In this implementation, the analyte sensor 252 can be used to detect whether any air is inadvertently leaking from the user's mouth and/or the user interface 120. In some implementations, the analyte sensor 252 is a volatile organic compound (VOC) sensor that can be used to detect carbon-based chemicals or compounds. In some implementations, the analyte sensor 174 can also be used to detect whether the user is breathing through their nose or mouth. For example, if the data output by an analyte sensor 252 positioned near the mouth of the user or within the facial mask (e.g., in implementations where the user interface 120 is a facial mask) detects the presence of an analyte, the control system 200 can use this data as an indication that the user is breathing through their mouth.

The moisture sensor 254 outputs data that can be stored in the memory device 204 and used by the control system 200. The moisture sensor 254 can be used to detect moisture in various areas surrounding the user (e.g., inside the conduit 140 or the user interface 120, near the user's face, near the connection between the conduit 140 and the user interface 120, near the connection between the conduit 140 and the respiratory therapy device 110, etc.). Thus, in some implementations, the moisture sensor 254 can be coupled to or integrated in the user interface 120 or in the conduit 140 to monitor the humidity of the pressurized air from the respiratory therapy device 110. In other implementations, the moisture sensor 254 is placed near any area where moisture levels need to be monitored. The moisture sensor 254 can also be used to monitor the humidity of the ambient environment surrounding the user, for example, the air inside the bedroom.

The Light Detection and Ranging (LiDAR) sensor 256 can be used for depth sensing. This type of optical sensor (e.g., laser sensor) can be used to detect objects and build three dimensional (3D) maps of the surroundings, such as of a living space. LiDAR can generally utilize a pulsed laser to make time of flight measurements. LiDAR is also referred to as 3D laser scanning. In an example of use of such a sensor, a fixed or mobile device (such as a smartphone) having a LiDAR sensor 256 can measure and map an area extending 5 meters or more away from the sensor. The LiDAR data can be fused with point cloud data estimated by an electromagnetic RADAR sensor, for example. The LiDAR sensor(s) 256 can also use artificial intelligence (AI) to automatically geofence RADAR systems by detecting and classifying features in a space that might cause issues for RADAR systems, such a glass windows (which can be highly reflective to RADAR). LiDAR can also be used to provide an estimate of the height of a person, as well as changes in height when the person sits down, or falls down, for example. LiDAR may be used to form a 3D mesh representation of an environment. In a further use, for solid surfaces through which radio waves pass (e.g., radio-translucent materials), the LiDAR may reflect off such surfaces, thus allowing a classification of different type of obstacles.

In some implementations, the one or more sensors 210 also include a galvanic skin response (GSR) sensor, a blood flow sensor, a respiration sensor, a pulse sensor, a sphygmomanometer sensor, an oximetry sensor, a sonar sensor, a RADAR sensor, a blood glucose sensor, a color sensor, a pH sensor, an air quality sensor, a tilt sensor, a rain sensor, a soil moisture sensor, a water flow sensor, an alcohol sensor, or any combination thereof.

While shown separately in FIG. 1, any combination of the one or more sensors 210 can be integrated in and/or coupled to any one or more of the components of the system 100, including the respiratory therapy device 110, the user interface 120, the conduit 140, the humidifier 160, the control system 200, the user device 260, the activity tracker 270, or any combination thereof. For example, the microphone 220 and the speaker 222 can be integrated in and/or coupled to the user device 260 and the pressure sensor 212 and/or flow rate sensor 132 are integrated in and/or coupled to the respiratory therapy device 110. In some implementations, at least one of the one or more sensors 210 is not coupled to the respiratory therapy device 110, the control system 200, or the user device 260, and is positioned generally adjacent to the user 20 during the sleep session (e.g., positioned on or in contact with a portion of the user 20, worn by the user 20, coupled to or positioned on the nightstand, coupled to the mattress, coupled to the ceiling, etc.).

One or more of the respiratory therapy device 110, the user interface 120, the conduit 140, the display device 150, and the humidifier 160 can contain one or more sensors (e.g., a pressure sensor, a flow rate sensor, or more generally any of the other sensors 210 described herein). These one or more sensors can be used, for example, to measure the air pressure and/or flow rate of pressurized air supplied by the respiratory therapy device 110.

The data from the one or more sensors 210 can be analyzed (e.g., by the control system 200) to determine one or more sleep-related parameters, which can include a respiration signal, a respiration rate, a respiration pattern, an inspiration amplitude, an expiration amplitude, an inspiration-expiration ratio, an occurrence of one or more events, a number of events per hour, a pattern of events, a sleep state, an apnea-hypopnea index (AHI), or any combination thereof. The one or more events can include snoring, apneas, central apneas, obstructive apneas, mixed apneas, hypopneas, a mask leak, a cough, a restless leg, a sleeping disorder, choking, an increased heart rate, labored breathing, an asthma attack, an epileptic episode, a seizure, increased blood pressure, or any combination thereof. Many of these sleep-related parameters are physiological parameters, although some of the sleep-related parameters can be considered to be non-physiological parameters. Other types of physiological and non-physiological parameters can also be determined, either from the data from the one or more sensors 210, or from other types of data.

The user device 260 (FIG. 1) includes a display device 262. The user device 260 can be, for example, a mobile device such as a smartphone, a tablet, a gaming console, a smart watch, a laptop, or the like. Alternatively, the user device 260 can be an external sensing system, a television (e.g., a smart television) or another smart home device (e.g., a smart speaker(s) such as Google Home, Amazon Echo, Alexa etc.). In some implementations, the user device is a wearable device (e.g., a smart watch). The display device 262 is generally used to display image(s) including still images, video images, or both. In some implementations, the display device 262 acts as a human-machine interface (HMI) that includes a graphic user interface (GUI) configured to display the image(s) and an input interface. The display device 262 can be an LED display, an OLED display, an LCD display, or the like. The input interface can be, for example, a touchscreen or touch-sensitive substrate, a mouse, a keyboard, or any sensor system configured to sense inputs made by a human user interacting with the user device 260. In some implementations, one or more user devices can be used by and/or included in the system 10.

In some implementations, the system 100 also includes an activity tracker 270. The activity tracker 270 is generally used to aid in generating physiological data associated with the user. The activity tracker 270 can include one or more of the sensors 210 described herein, such as, for example, the motion sensor 138 (e.g., one or more accelerometers and/or gyroscopes), the PPG sensor 154, and/or the ECG sensor 156. The physiological data from the activity tracker 270 can be used to determine, for example, a number of steps, a distance traveled, a number of steps climbed, a duration of physical activity, a type of physical activity, an intensity of physical activity, time spent standing, a respiration rate, an average respiration rate, a resting respiration rate, a maximum he respiration art rate, a respiration rate variability, a heart rate, an average heart rate, a resting heart rate, a maximum heart rate, a heart rate variability, a number of calories burned, blood oxygen saturation, electrodermal activity (also known as skin conductance or galvanic skin response), or any combination thereof. In some implementations, the activity tracker 270 is coupled (e.g., electronically or physically) to the user device 260.

In some implementations, the activity tracker 270 is a wearable device that can be worn by the user, such as a smartwatch, a wristband, a ring, or a patch. For example, referring to FIG. 2, the activity tracker 270 is worn on a wrist of the user 20. The activity tracker 270 can also be coupled to or integrated a garment or clothing that is worn by the user. Alternatively still, the activity tracker 270 can also be coupled to or integrated in (e.g., within the same housing) the user device 260. More generally, the activity tracker 270 can be communicatively coupled with, or physically integrated in (e.g., within a housing), the control system 200, the memory device 204, the respiratory therapy system 100, and/or the user device 260.

In some implementations, the system 100 also includes a blood pressure device 280. The blood pressure device 280 is generally used to aid in generating cardiovascular data for determining one or more blood pressure measurements associated with the user 20. The blood pressure device 280 can include at least one of the one or more sensors 210 to measure, for example, a systolic blood pressure component and/or a diastolic blood pressure component.

In some implementations, the blood pressure device 280 is a sphygmomanometer including an inflatable cuff that can be worn by the user 20 and a pressure sensor (e.g., the pressure sensor 212 described herein). For example, in the example of FIG. 2, the blood pressure device 280 can be worn on an upper arm of the user 20. In such implementations where the blood pressure device 280 is a sphygmomanometer, the blood pressure device 280 also includes a pump (e.g., a manually operated bulb) for inflating the cuff. In some implementations, the blood pressure device 280 is coupled to the respiratory therapy device 110 of the respiratory therapy system 100, which in turn delivers pressurized air to inflate the cuff. More generally, the blood pressure device 280 can be communicatively coupled with, and/or physically integrated in (e.g., within a housing), the control system 200, the memory device 204, the respiratory therapy system 100, the user device 260, and/or the activity tracker 270.

In other implementations, the blood pressure device 280 is an ambulatory blood pressure monitor communicatively coupled to the respiratory therapy system 100. An ambulatory blood pressure monitor includes a portable recording device attached to a belt or strap worn by the user 20 and an inflatable cuff attached to the portable recording device and worn around an arm of the user 20. The ambulatory blood pressure monitor is configured to measure blood pressure between about every fifteen minutes to about thirty minutes over a 24-hour or a 48-hour period. The ambulatory blood pressure monitor may measure heart rate of the user 20 at the same time. These multiple readings are averaged over the 24-hour period. The ambulatory blood pressure monitor determines any changes in the measured blood pressure and heart rate of the user 20, as well as any distribution and/or trending patterns of the blood pressure and heart rate data during a sleeping period and an awakened period of the user 20. The measured data and statistics may then be communicated to the respiratory therapy system 100.

The blood pressure device 280 maybe positioned external to the respiratory therapy system 100, coupled directly or indirectly to the user interface 120, coupled directly or indirectly to a headgear associated with the user interface 120, or inflatably coupled to or about a portion of the user 20. The blood pressure device 280 is generally used to aid in generating physiological data for determining one or more blood pressure measurements associated with a user, for example, a systolic blood pressure component and/or a diastolic blood pressure component. In some implementations, the blood pressure device 280 is a sphygmomanometer including an inflatable cuff that can be worn by a user and a pressure sensor (e.g., the pressure sensor 212 described herein).

In some implementations, the blood pressure device 280 is an invasive device which can continuously monitor arterial blood pressure of the user 20 and take an arterial blood sample on demand for analyzing gas of the arterial blood. In some other implementations, the blood pressure device 280 is a continuous blood pressure monitor, using a radio frequency sensor and capable of measuring blood pressure of the user 20 once very few seconds (e.g., every 3 seconds, every 5 seconds, every 7 seconds, etc.) The radio frequency sensor may use continuous wave, frequency-modulated continuous wave (FMCW with ramp chirp, triangle, sinewave), other schemes such as PSK, FSK etc., pulsed continuous wave, and/or spread in ultra wideband ranges (which may include spreading, PRN codes or impulse systems).

While the control system 200 and the memory device 204 are described and shown in FIG. 1 as being a separate and distinct component of the system 100, in some implementations, the control system 200 and/or the memory device 204 are integrated in the user device 260 and/or the respiratory therapy device 110. Alternatively, in some implementations, the control system 200 or a portion thereof (e.g., the processor 202) can be located in a cloud (e.g., integrated in a server, integrated in an Internet of Things (IoT) device, connected to the cloud, be subject to edge cloud processing, etc.), located in one or more servers (e.g., remote servers, local servers, etc.), or any combination thereof.

While system 100 is shown as including all of the components described above, more or fewer components can be included in a system according to implementations of the present disclosure. For example, a first alternative system includes the control system 200, the memory device 204, and at least one of the one or more sensors 210 and does not include the respiratory therapy system 100. As another example, a second alternative system includes the control system 200, the memory device 204, at least one of the one or more sensors 210, and the user device 260. As yet another example, a third alternative system includes the control system 200, the memory device 204, the respiratory therapy system 100, at least one of the one or more sensors 210, and the user device 260. Thus, various systems can be formed using any portion or portions of the components shown and described herein and/or in combination with one or more other components.

As used herein, a sleep session can be defined in multiple ways. For example, a sleep session can be defined by an initial start time and an end time. In some implementations, a sleep session is a duration where the user is asleep, that is, the sleep session has a start time and an end time, and during the sleep session, the user does not wake until the end time. That is, any period of the user being awake is not included in a sleep session. From this first definition of sleep session, if the user wakes ups and falls asleep multiple times in the same night, each of the sleep intervals separated by an awake interval is a sleep session.

Alternatively, in some implementations, a sleep session has a start time and an end time, and during the sleep session, the user can wake up, without the sleep session ending, so long as a continuous duration that the user is awake is below an awake duration threshold. The awake duration threshold can be defined as a percentage of a sleep session. The awake duration threshold can be, for example, about twenty percent of the sleep session, about fifteen percent of the sleep session duration, about ten percent of the sleep session duration, about five percent of the sleep session duration, about two percent of the sleep session duration, etc., or any other threshold percentage. In some implementations, the awake duration threshold is defined as a fixed amount of time, such as, for example, about one hour, about thirty minutes, about fifteen minutes, about ten minutes, about five minutes, about two minutes, etc., or any other amount of time.

In some implementations, a sleep session is defined as the entire time between the time in the evening at which the user first entered the bed, and the time the next morning when user last left the bed. Put another way, a sleep session can be defined as a period of time that begins on a first date (e.g., Monday, Jan. 6, 2020) at a first time (e.g., 10:00 PM), that can be referred to as the current evening, when the user first enters a bed with the intention of going to sleep (e.g., not if the user intends to first watch television or play with a smartphone before going to sleep, etc.), and ends on a second date (e.g., Tuesday, Jan. 7, 2020) at a second time (e.g., 7:00 AM), that can be referred to as the next morning, when the user first exits the bed with the intention of not going back to sleep that next morning.

In some implementations, the user can manually define the beginning of a sleep session and/or manually terminate a sleep session. For example, the user can select (e.g., by clicking or tapping) one or more user-selectable element that is displayed on the display device 262 of the user device 260 (FIG. 1) to manually initiate or terminate the sleep session.

Generally, the sleep session includes any point in time after the user 20 has laid or sat down in the bed 40 (or another area or object on which they intend to sleep), and has turned on the respiratory therapy device 110 and donned the user interface 120. The sleep session can thus include time periods (i) when the user 20 is using the respiratory therapy system 100, but before the user 20 attempts to fall asleep (for example when the user 20 lays in the bed 40 reading a book); (ii) when the user 20 begins trying to fall asleep but is still awake; (iii) when the user 20 is in a light sleep (also referred to as stage 1 and stage 2 of non-rapid eye movement (NREM) sleep); (iv) when the user 20 is in a deep sleep (also referred to as slow-wave sleep, SWS, or stage 3 of NREM sleep); (v) when the user 20 is in rapid eye movement (REM) sleep; (vi) when the user 20 is periodically awake between light sleep, deep sleep, or REM sleep; or (vii) when the user 20 wakes up and does not fall back asleep.

The sleep session is generally defined as ending once the user 20 removes the user interface 120, turns off the respiratory therapy device 110, and gets out of bed 40. In some implementations, the sleep session can include additional periods of time, or can be limited to only some of the above-disclosed time periods. For example, the sleep session can be defined to encompass a period of time beginning when the respiratory therapy device 110 begins supplying the pressurized air to the airway or the user 20, ending when the respiratory therapy device 110 stops supplying the pressurized air to the airway of the user 20, and including some or all of the time points in between, when the user 20 is asleep or awake.

Figure 7:
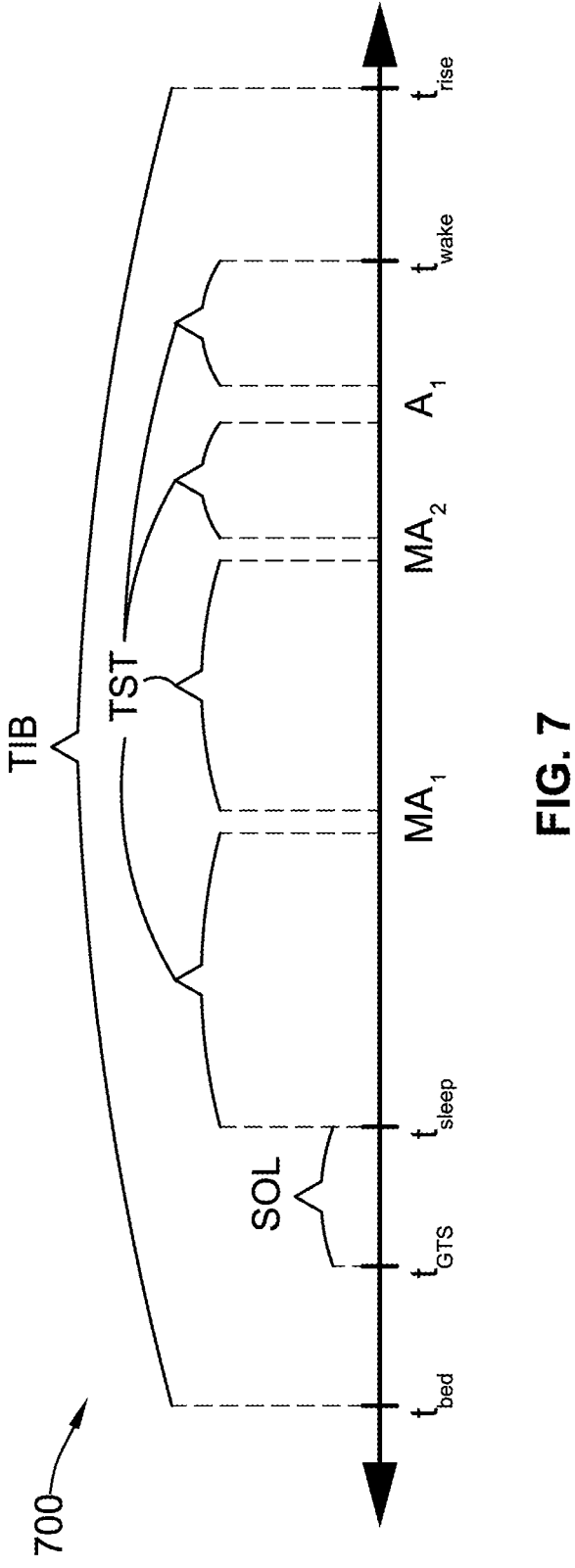
FIG. 7 illustrates an exemplary timeline for a sleep session, according to some implementations of the present disclosure.

Referring to the timeline 700 in FIG. 7 the enter bed time $t_{bed}$ is associated with the time that the user initially enters the bed (e.g., bed 40 in FIG. 2) prior to falling asleep (e.g., when the user lies down or sits in the bed). The enter bed time $t_{bed}$ can be identified based on a bed threshold duration to distinguish between times when the user enters the bed for sleep and when the user enters the bed for other reasons (e.g., to watch TV). For example, the bed threshold duration can be at least about 10 minutes, at least about 20 minutes, at least about 30 minutes, at least about 45 minutes, at least about 1 hour, at least about 2 hours, etc. While the enter bed time $t_{bed}$ is described herein in reference to a bed, more generally, the enter time $t_{bed}$ can refer to the time the user initially enters any location for sleeping (e.g., a couch, a chair, a sleeping bag, etc.).

The go-to-sleep time (GTS) is associated with the time that the user initially attempts to fall asleep after entering the bed ($t_{bed}$). For example, after entering the bed, the user may engage in one or more activities to wind down prior to trying to sleep (e.g., reading, watching TV, listening to music, using the user device 260, etc.). The initial sleep time ($t_{sleep}$) is the time that the user initially falls asleep. For example, the initial sleep time ($t_{sleep}$) can be the time that the user initially enters the first non-REM sleep stage.

The wake-up time $t_{wake}$ is the time associated with the time when the user wakes up without going back to sleep (e.g., as opposed to the user waking up in the middle of the night and going back to sleep). The user may experience one of more unconscious microawakenings (e.g., microawakenings $MA_1$ and $MA_2$) having a short duration (e.g., 5 seconds, 10 seconds, 30 seconds, 1 minute, etc.) after initially falling asleep. In contrast to the wake-up time $t_{wake}$, the user goes back to sleep after each of the microawakenings $MA_1$ and $MA_2$. Similarly, the user may have one or more conscious awakenings (e.g., awakening A) after initially falling asleep (e.g., getting up to go to the bathroom, attending to children or pets, sleep walking, etc.). However, the user goes back to sleep after the awakening A. Thus, the wake-up time $t_{wake}$ can be defined, for example, based on a wake threshold duration (e.g., the user is awake for at least 15 minutes, at least 20 minutes, at least 30 minutes, at least 1 hour, etc.).

Similarly, the rising time $t_{rise}$ is associated with the time when the user exits the bed and stays out of the bed with the intent to end the sleep session (e.g., as opposed to the user getting up during the night to go to the bathroom, to attend to children or pets, sleep walking, etc.). In other words, the rising time $t_{rise}$ is the time when the user last leaves the bed without returning to the bed until a next sleep session (e.g., the following evening). Thus, the rising time $t_{rise}$ can be defined, for example, based on a rise threshold duration (e.g., the user has left the bed for at least 15 minutes, at least 20 minutes, at least 30 minutes, at least 1 hour, etc.). The enter bed time $t_{bed}$ time for a second, subsequent sleep session can also be defined based on a rise threshold duration (e.g., the user has left the bed for at least 4 hours, at least 6 hours, at least 8 hours, at least 12 hours, etc.).

As described above, the user may wake up and get out of bed one more times during the night between the initial $t_{bed}$ and the final $t_{rise}$. In some implementations, the final wake-up time $t_{wake}$ and/or the final rising time $t_{rise}$ that are identified or determined based on a predetermined threshold duration of time subsequent to an event (e.g., falling asleep or leaving the bed). Such a threshold duration can be customized for the user. For a standard user which goes to bed in the evening, then wakes up and goes out of bed in the morning any period (between the user waking up ($t_{wake}$) or raising up ($t_{rise}$), and the user either going to bed ($t_{bed}$), going to sleep ($t_{GTS}$) or falling asleep ($t_{sleep}$) of between about 12 and about 18 hours can be used. For users that spend longer periods of time in bed, shorter threshold periods may be used (e.g., between about 8 hours and about 14 hours). The threshold period may be initially selected and/or later adjusted based on the system monitoring the user's sleep behavior.

The total time in bed (TIB) is the duration of time between the time enter bed time $t_{bed}$ and the rising time $t_{rise}$. The total sleep time (TST) is associated with the duration between the initial sleep time and the wake-up time, excluding any conscious or unconscious awakenings and/or micro-awakenings therebetween. Generally, the total sleep time (TST) will be shorter than the total time in bed (TIB) (e.g., one minute short, ten minutes shorter, one hour shorter, etc.). For example, referring to the timeline 700 of FIG. 7, the total sleep time (TST) spans between the initial sleep time $t_{sleep}$ and the wake-up time $t_{wake}$, but excludes the duration of the first micro-awakening $MA_1$, the second micro-awakening $MA_2$, and the awakening A. As shown, in this example, the total sleep time (TST) is shorter than the total time in bed (TIB).

In some implementations, the total sleep time (TST) can be defined as a persistent total sleep time (PTST). In such implementations, the persistent total sleep time excludes a predetermined initial portion or period of the first non-REM stage (e.g., light sleep stage). For example, the predetermined initial portion can be between about 30 seconds and about 20 minutes, between about 1 minute and about 10 minutes, between about 3 minutes and about 5 minutes, etc. The persistent total sleep time is a measure of sustained sleep, and smooths the sleep-wake hypnogram. For example, when the user is initially falling asleep, the user may be in the first non-REM stage for a very short time (e.g., about 30 seconds), then back into the wakefulness stage for a short period (e.g., one minute), and then goes back to the first non-REM stage. In this example, the persistent total sleep time excludes the first instance (e.g., about 30 seconds) of the first non-REM stage.

In some implementations, the sleep session is defined as starting at the enter bed time ($t_{bed}$) and ending at the rising time ($t_{rise}$), i.e., the sleep session is defined as the total time in bed (TIB). In some implementations, a sleep session is defined as starting at the initial sleep time ($t_{sleep}$) and ending at the wake-up time ($t_{wake}$). In some implementations, the sleep session is defined as the total sleep time (TST). In some implementations, a sleep session is defined as starting at the go-to-sleep time ($t_{GTS}$) and ending at the wake-up time ($t_{wake}$). In some implementations, a sleep session is defined as starting at the go-to-sleep time ($t_{GTS}$) and ending at the rising time ($t_{rise}$). In some implementations, a sleep session is defined as starting at the enter bed time ($t_{bed}$) and ending at the wake-up time ($t_{wake}$). In some implementations, a sleep session is defined as starting at the initial sleep time ($t_{sleep}$) and ending at the rising time ($t_{rise}$).

Figure 8:
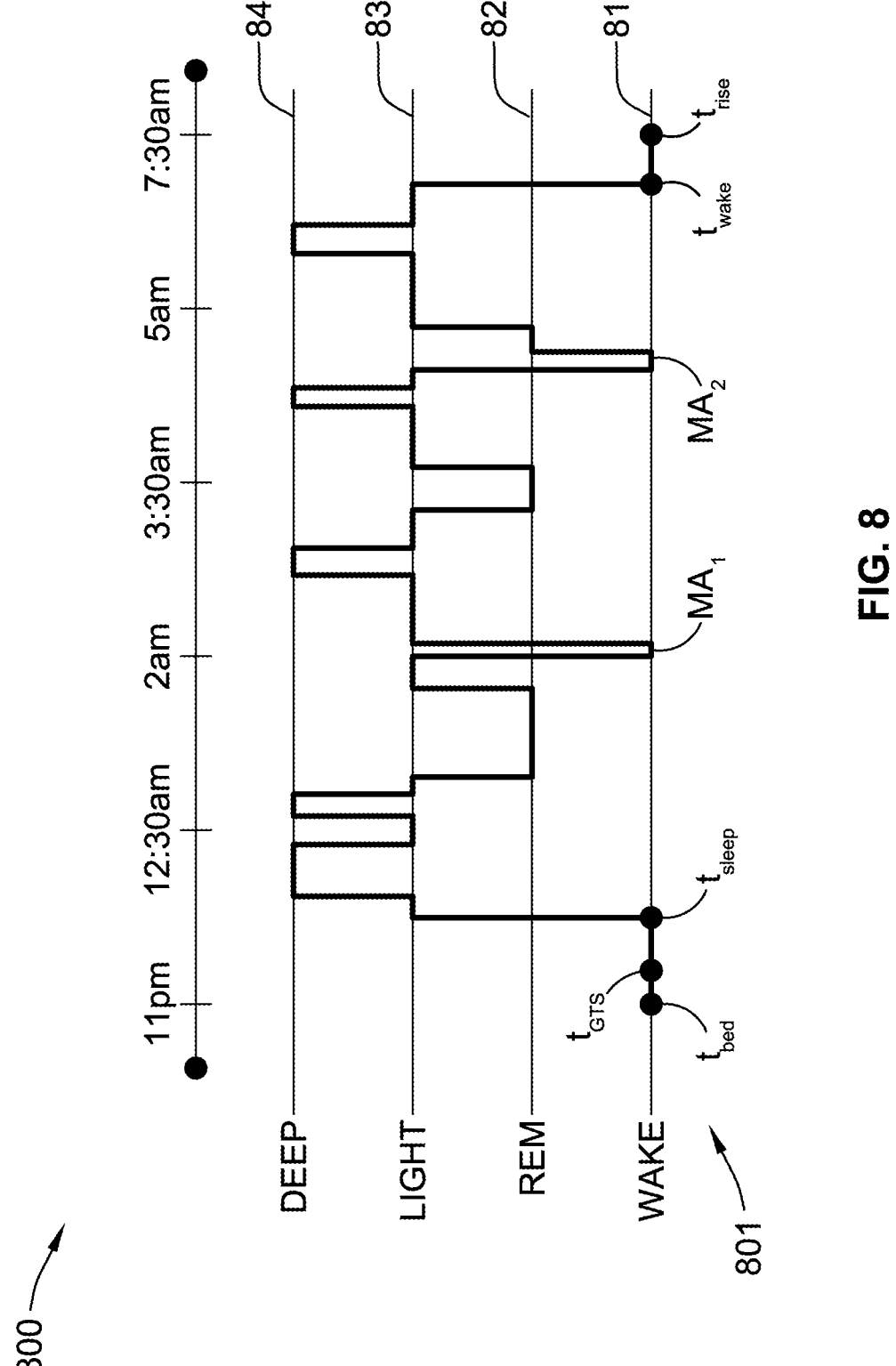
FIG. 8 illustrates an exemplary hypnogram associated with the sleep session of FIG. 7, according to some implementations of the present disclosure.

Referring to FIG. 8, an exemplary hypnogram 800 corresponding to the timeline 700 (FIG. 7), according to some implementations, is illustrated. As shown, the hypnogram 800 includes a sleep-wake signal 801, a wakefulness stage axis 810, a REM stage axis 820, a light sleep stage axis 830, and a deep sleep stage axis 840. The intersection between the sleep-wake signal 801 and one of the axes 810-840 is indicative of the sleep stage at any given time during the sleep session.

The sleep-wake signal 801 can be generated based on physiological data associated with the user (e.g., generated by one or more of the sensors 210 described herein). The sleep-wake signal can be indicative of one or more sleep states, including wakefulness, relaxed wakefulness, micro-awakenings, a REM stage, a first non-REM stage, a second non-REM stage, a third non-REM stage, or any combination thereof. In some implementations, one or more of the first non-REM stage, the second non-REM stage, and the third non-REM stage can be grouped together and categorized as a light sleep stage or a deep sleep stage. For example, the light sleep stage can include the first non-REM stage and the deep sleep stage can include the second non-REM stage and the third non-REM stage. While the hypnogram 800 is shown in FIG. 8 as including the light sleep stage axis 830 and the deep sleep stage axis 840, in some implementations, the hypnogram 800 can include an axis for each of the first non-REM stage, the second non-REM stage, and the third non-REM stage. In other implementations, the sleep-wake signal can also be indicative of a respiration signal, a respiration rate, an inspiration amplitude, an expiration amplitude, an inspiration-expiration ratio, a number of events per hour, a pattern of events, or any combination thereof. Information describing the sleep-wake signal can be stored in the memory device 204.

The hypnogram 800 can be used to determine one or more sleep-related parameters, such as, for example, a sleep onset latency (SOL), wake-after-sleep onset (WASO), a sleep efficiency (SE), a sleep fragmentation index, sleep blocks, or any combination thereof.

The sleep onset latency (SOL) is defined as the time between the go-to-sleep time ($t_{GTS}$) and the initial sleep time ($t_{sleep}$). In other words, the sleep onset latency is indicative of the time that it took the user to actually fall asleep after initially attempting to fall asleep. In some implementations, the sleep onset latency is defined as a persistent sleep onset latency (PSOL). The persistent sleep onset latency differs from the sleep onset latency in that the persistent sleep onset latency is defined as the duration time between the go-to-sleep time and a predetermined amount of sustained sleep. In some implementations, the predetermined amount of sustained sleep can include, for example, at least 10 minutes of sleep within the second non-REM stage, the third non-REM stage, and/or the REM stage with no more than 2 minutes of wakefulness, the first non-REM stage, and/or movement therebetween. In other words, the persistent sleep onset latency requires up to, for example, 8 minutes of sustained sleep within the second non-REM stage, the third non-REM stage, and/or the REM stage. In other implementations, the predetermined amount of sustained sleep can include at least 10 minutes of sleep within the first non-REM stage, the second non-REM stage, the third non-REM stage, and/or the REM stage subsequent to the initial sleep time. In such implementations, the predetermined amount of sustained sleep can exclude any micro-awakenings (e.g., a ten second micro-awakening does not restart the 10-minute period).

The wake-after-sleep onset (WASO) is associated with the total duration of time that the user is awake between the initial sleep time and the wake-up time. Thus, the wake-after-sleep onset includes short and micro-awakenings during the sleep session (e.g., the micro-awakenings $MA_1$ and $MA_2$ shown in FIG. 7), whether conscious or unconscious. In some implementations, the wake-after-sleep onset (WASO) is defined as a persistent wake-after-sleep onset (PWASO) that only includes the total durations of awakenings having a predetermined length (e.g., greater than 10 seconds, greater than 30 seconds, greater than 60 seconds, greater than about 5 minutes, greater than about 10 minutes, etc.)

The sleep efficiency (SE) is determined as a ratio of the total time in bed (TIB) and the total sleep time (TST). For example, if the total time in bed is 8 hours and the total sleep time is 7.5 hours, the sleep efficiency for that sleep session is 93.75%. The sleep efficiency is indicative of the sleep hygiene of the user. For example, if the user enters the bed and spends time engaged in other activities (e.g., watching TV) before sleep, the sleep efficiency will be reduced (e.g., the user is penalized). In some implementations, the sleep efficiency (SE) can be calculated based on the total time in bed (TIB) and the total time that the user is attempting to sleep. In such implementations, the total time that the user is attempting to sleep is defined as the duration between the go-to-sleep (GTS) time and the rising time described herein. For example, if the total sleep time is 8 hours (e.g., between 11 PM and 7 AM), the go-to-sleep time is 10:45 PM, and the rising time is 7:15 AM, in such implementations, the sleep efficiency parameter is calculated as about 94%.

The fragmentation index is determined based at least in part on the number of awakenings during the sleep session. For example, if the user had two micro-awakenings (e.g., micro-awakening $MA_1$ and micro-awakening $MA_2$ shown in FIG. 7), the fragmentation index can be expressed as 2. In some implementations, the fragmentation index is scaled between a predetermined range of integers (e.g., between 0 and 10).

The sleep blocks are associated with a transition between any stage of sleep (e.g., the first non-REM stage, the second non-REM stage, the third non-REM stage, and/or the REM) and the wakefulness stage. The sleep blocks can be calculated at a resolution of, for example, 30 seconds.

In some implementations, the systems and methods described herein can include generating or analyzing a hypnogram including a sleep-wake signal to determine or identify the enter bed time ($t_{bed}$), the go-to-sleep time ($t_{GTS}$), the initial sleep time ($t_{sleep}$), one or more first micro-awakenings (e.g., $MA_1$ and $MA_2$), the wake-up time ($t_{wake}$), the rising time ($t_{rise}$), or any combination thereof based at least in part on the sleep-wake signal of a hypnogram.

In other implementations, one or more of the sensors 210 can be used to determine or identify the enter bed time ($t_{bed}$), the go-to-sleep time ($t_{GTS}$), the initial sleep time ($t_{sleep}$), one or more first micro-awakenings (e.g., $MA_1$ and $MA_2$), the wake-up time ($t_{wake}$), the rising time ($t_{rise}$), or any combination thereof, which in turn define the sleep session. For example, the enter bed time $t_{bed}$ can be determined based on, for example, data generated by the motion sensor 218, the microphone 220, the camera 232, or any combination thereof. The go-to-sleep time can be determined based on, for example, data from the motion sensor 218 (e.g., data indicative of no movement by the user), data from the camera 232 (e.g., data indicative of no movement by the user and/or that the user has turned off the lights) data from the microphone 220 (e.g., data indicative of the using turning off a TV), data from the user device 260 (e.g., data indicative of the user no longer using the user device 260), data from the pressure sensor 212 and/or the flow rate sensor 214 (e.g., data indicative of the user turning on the respiratory therapy device 110, data indicative of the user donning the user interface 120, etc.), or any combination thereof.

Figure 9:
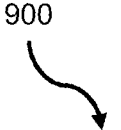
FIG. 9 is a process flow diagram for a method for monitoring a user's interaction and maintaining interest of the user, according to some implementations of the present disclosure.
Figure 9:
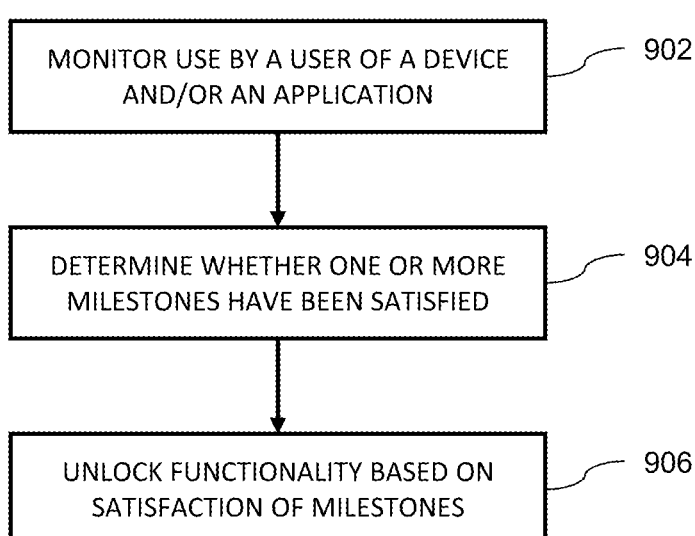

Referring to FIG. 9, a method 900 for monitoring user interaction with a device, with an application associated with the device, or a combination thereof and maintaining interest of a user is illustrated, according to some implementations of the present disclosure. One or more steps of the method 900 can be implemented by any element of the system 10 described herein, such as the respiratory therapy system 100, the respiratory therapy device 110, the control system 200, and/or the user device 260.

At step 902, the element of the system 10 implementing the method 900 monitors use by a user of a device, of an application associated with the device, or a combination thereof. The device is configured to provide therapy to the user. For example, the device can be a respiratory therapy system (e.g., respiratory therapy system 100), which can include a respiratory therapy device (e.g., respiratory therapy device 110). However, the device can be any device that provides therapy to a user, such as any other medical device. According to some implementations, providing the therapy includes providing discrete sessions of therapy over a period of time. In the context of a respiratory therapy system, providing the therapy includes providing PAP during sleeps sessions over the course of many days, such as several weeks, several months, several years, and even longer. Over that period of time, the user may lose interest in the therapy such that the method 900 helps maintain the interest of the user in the therapy and, consequently, one or both of the device that is configured to provide the therapy and the application, which is further described below.

According to some implementations, and as disclosed further below, the method 900 may monitor use of the device or the application or both to determine whether the user is at risk of losing interest in therapy (e.g., usage is less than x number of hours per day, or frequency of use is less than n times per week, etc.), or at risk of losing interest in interacting with the application during and/or related to therapy, and intervene to bring the user back on therapy or continue usage. For example, if the usage is determined to be below a threshold, a notification may be sent to encourage continued use or to invite the user to sign up to access for additional functions or richer settings of the device, the application, or a combination thereof. The method 900 may also help in elevating user's experience by increasing engagement or interaction with the user though one or both of the device and the application.

According to some implementations, the monitoring can be cumulative such that usage of the device, the application, or both is tracked over time, such as being logged or stored for further analysis. Cumulative monitoring allows for tracking certain aspects of the usage over various periods of time, such as indefinitely, the lifetime of the device, a number of years, a number of months, a number of days, a number of sleep sessions, etc. According to some implementations, the monitoring can be instantaneous in the sense that usage of the device, the application, or both is determined only for analysis of a specific, present timeframe such that logging or storing the usage is not necessary. According to some implementations, the monitoring can include a combination of cumulative monitoring, such as logging or storing certain aspects of usage of the device, the application, or both over time, and present monitoring, such as determining certain different aspects of the usage of the device, the application, or both for a present timeframe but no logging or storing that usage.

The application is configured to provide control of the device, to provide information to the user related to the therapy, or a combination thereof. For example, the user may control the device entirely through the application, or through the application in combination with the device, or as an alternative to entirely through the device. In addition or in the alternative to providing control of the device, the application can provide information regarding the therapy obtained by or with the device. The information can be any information related to the therapy, such as settings or metrics related to the therapy, how the therapy is improving the wellbeing of the user, how the therapy is progressing in general, milestones the user should be achieving to stay on track with the therapy, further insights on how to improve therapy, etc.

At step 904, the element of the system 10 implementing the method 900 determines whether one or more milestones associated with an incentive scheme for the user have been satisfied by the use. The incentive scheme relates to continued provisioning of the therapy to the user by the device. More specifically, the incentive scheme relates to the continued provisioning of the therapy to the user by the device within the context of the user using the device, using the application, or a combination thereof. Similarly, the one or more milestones relate to user compliance with respect to usage of the device, usage of the application, or a combination thereof, within the context of the continued provisioning of the therapy to the user by the device. Usage of the device or usage of the application may include duration of use, frequency of user's interaction with the device or application, or a combination of both. Thus, the incentive scheme is, in part, a foundation for maintaining interest of the user by providing additional functionality, discussed in greater detail below, as the user achieves one or more of the one or more milestones. The additional functionality keeps the use of the device, the application, or both fresh or provides greater information to the user, and that information provides additional interest for the user.

According to some implementations, the one or more milestones can also apply to one or more other users. In which case, step 904 can further include the sub-steps of the element of the system 10 implementing the method 900 comparing satisfaction of the one or more milestones associated with the incentive scheme for the user with satisfaction of the one or more milestones associated with one or more incentive schemes of one or more other users. The element of the system 10 implementing the method 900 can further provide a reward to the user, at least one of the one or more other users, or a combination based on the comparison and which of the one or more milestones have been satisfied by which of the user and the one or more other users. These two sub-steps of step 904 can be done alone or in combination with the subsequent step 906 discussed below. Thus, in one or more implementations, the method 900 can end after completion of the sub-steps within step 904. Alternatively, the method 900 can proceed with step 906. These sub-steps add an element of competition between the user and the one or more other users. The competition can further provide interest in the user or the one or more other users in maintaining or increasing use of the device, the application, or both.

According to some implementations, the user and the one or more other users may know each other, such as being family members, friends, acquaintances, etc., or they may not know each other. Whether the user knows the one or more other users can aid in maintaining interest of the user in the device, the application, or a combination thereof, such as the user wanting to compete with family members or wanting to compete with strangers. For example, strangers may provide a more competitive environment for the user.

At step 906, the element of the system 10 implementing the method 900 unlocks functionality of the device, the application associated with the device, or a combination thereof for the user based on satisfaction of at least one of the one or more milestones. Unlocking the functionality of the device, the application associated with the device, or a combination thereof maintains the interest by the user by maintaining the interest of the user for the device, the application, or a combination thereof.

In one or more implementations, the unlocked functionality includes providing more granular control of the therapy by the device, providing one or more additional features for the therapy provided by the device, or a combination thereof. According to some implementations, the one or more additional features for the therapy are non-critical features. Critical features for the therapy are the base features required for providing therapy according to a baseline therapy. Thus, by default, the non-critical features are not required to provide the baseline therapy. Instead, the non-critical features are features that can be added to improve the baseline therapy. Improving therapy can include providing more personalized therapy than the baseline therapy, because the baseline therapy generally applies to all users. Thus, the one or more non-critical additional features include features that allow for personalization of the therapy. The one or more non-critical additional features can also allow for comfortable therapy. For example, in the case of a respiratory therapy system, the one or more non-critical additional features can include adding control over humidification or temperature control for the air supplied to the user during PAP therapy, control over ramp pressure and duration, expiratory pressure relief (EPR), and the like. The non-critical features, such as duration of the ramp settings, for example, is fixed at 15-, 30- or 45-minutes increment. In some implementations, the unlocked functionality includes providing richer therapy settings which allows for granular adjustment of the ramp duration, for example, at 5-minutes increment. The unlocked functionality, for example, provides granular control of other non-critical features or settings of the device, application, or both.

In one or more implementations, the unlocked functionality includes one or more ways of visualizing existing data on the device, on the application, or a combination thereof. The standard ways of visualizing data that come on the device or the application or both may visualize the data according to a baseline. However, this baseline, while presenting the basic information to the user may not generate any interest in the user. Thus, the one or more ways of visualizing existing data may vary from the baseline such that they generate interest in the user, by being more aesthetically pleasing, more intuitive, and the like.

In one or more implementations, the unlocked functionality includes providing access to premium data on the device, on the application, or a combination thereof. Similar to the critical vs. non-critical features and the ways of presenting data, the data itself may be categorized generally into at least two categories, baseline data that is needed to understand what is occurring during therapy, such as to make sure settings and/or parameters needed to be set for the therapy are correctly set. In addition, premium data can provide elevated understanding of what is occurring during therapy or what is being achieved by therapy or both, such as being more granular or more insightful.

In one or more implementations, the unlocked functionality includes changing one or more stylistic appearances of the device, of the application, or a combination thereof. The one or more stylistic appearances of the device can include one or more stylistic appearances of a housing of the device, of a user interface of the device, or a combination thereof. For example, the housing of the device may have different colors of LED lights, and the unlocked functionality may include access to controlling the LED light of different colors. The unlocked functionality can in addition or in the alternative provide control over the appearance of the user interface.

In one or more implementations, the unlocked functionality includes providing access to, control over, or a combination thereof one or more other devices through the application. For example, the one or more other devices can be devices directly or indirectly related to providing therapy. In the case of PAP, the devices directly related to providing therapy can be, for example, other devices within the respiratory therapy system, such as a device that controls humidification, a device that controls the supply of an agent into the pressurized air, and the like. In the case of PAP, the devices indirectly related to providing therapy can be, for example, the HVAC devices, which may indirectly control the temperature and or humidity of the pressurized air, lights, televisions, or any other Internet-of-things devices.

In one or more implementations, the unlocked functionality includes pairing the device with a smartphone of the user to allow the device to receive additional information from the smartphone. The additional information can unlock further functionality on the device. The additional information from the smartphone can include Global Positioning System (GPS) information for automatically setting functionality of the device based on environmental conditions associated with the GPS information. According to some implementations, the device does not have access to the additional information without pairing the device with the smartphone. According to some implementations, the application executes on the smartphone, and the additional information includes physiological information of the user determined by the smartphone, user identification information provided by the user through the smartphone, or a combination thereof. According to some implementations, the additional information can be health and related personal information from the user, including, for example, energy level, number of steps walked, location of home and/or work. The additional information can be actively provided to the smartphone or passively provided or collected by the smartphone. According to some aspects, providing the additional information from the smartphone allows the device to be simpler or compact because information is received from the smartphone rather than generated/acquired by the device with the corresponding need to a related sensor.

In one or more implementations, the unlocked functionality includes providing latest news or media contents related to the device, the application, the therapy provided by the device, or a combination thereof.

In one or more implementations, the unlocked functionality includes accessing software updates for the device, the application, or a combination thereof. The provided access to the software update may include providing access that would not otherwise be provided. Alternatively, the provided access may instead be access that is provided a certain period of time before access would otherwise be provided, such as month early.

In one or more implementations, the element of the system 10 implementing the method 900 can unlock one or more rewards associated with one or more participating businesses, such as discounts on new products, for the user based on satisfaction of the at least one of the one or more milestones. This can occur in addition to step 906 or in the alternative to step 906. While the above functionality that is unlocked generally relates to the providing of therapy to the user as the reward, alternatively or in addition, the reward can be a reward unrelated to the providing of therapy.

The unlocked functionally discussed above can be unlocked once and thereafter be accessed. Alternatively, the unlocked functionality may be unlocked for a period of time and then revert back to a locked state such that the user has to achieve another milestone to again unlock the functionality. For example, in the case of providing software updates for the device, the application, or a combination thereof, separate milestones may be related to a specific, separate software updates. Alternatively, a single milestone can relate to all software update. Whether milestones are permanent or expire after a certain period of time can depend on the patient. If the patient becomes complacent and begins to stop using the application and/or the device, the milestones may be reset so that the user has to regain the functionality. However, the user can receive messages regarding the loss of the functionality along with motivation to help the user regain the functionality. The messages can be the equivalent of a coach helping to coach the user back into compliance with the incentive scheme.

ALTERNATIVE IMPLEMENTATION SECTION

Implementation 1. A method comprising: monitoring use by a user of a device, of an application associated with the device, or a combination thereof, the device providing therapy to the user, and the application providing control of the device, providing information to the user related to the therapy, or a combination thereof, determining whether one or more milestones associated with an incentive scheme for the user have been satisfied by the use, the incentive scheme relating to continued provisioning of the therapy to the user by the device; and unlocking functionality of the device, the application associated with the device, or a combination thereof for the user based on satisfaction of at least one of the one or more milestones.

Implementation 2. The method of implementation 1, wherein the functionality includes: i. providing more granular control of the therapy by the device, providing one or more additional features for the therapy provided by the device, or a combination thereof, ii. one or more ways of visualizing existing data on the device, on the application, or a combination thereof, iii. providing access to premium data on the device, on the application, or a combination thereof, iv. changing one or more stylistic appearances of the device, of the application, or a combination thereof; v. providing access to, control over, or a combination thereof one or more other devices through the application; vi. pairing the device with a smartphone of the user to allow the device to receive additional information from the smartphone, the information unlocking further functionality on the device; vii. providing latest news related to the device, the application, the therapy provided by the device, or a combination thereof; and/or viii. accessing software updates for the device, the application, or a combination thereof.

Implementation 3. The method of implementation 2, wherein the one or more stylistic appearances of the device include one or more stylistic appearances of a housing of the device, of a user interface of the device, or a combination thereof.

Implementation 4. The method of implementation 2, wherein the additional information from the smartphone includes Global Positioning System (GPS) information for automatically setting functionality of the device based on environmental conditions associated with the GPS information.

Implementation 5. The method of implementation 2, wherein the device does not have access to the additional information without the pairing of the device with the smartphone.

Implementation 6. The method of implementation 2, wherein the application executes on the smartphone, and the additional information includes physiological information of the user determined by the smartphone, user identification information provided by the user through the smartphone, or a combination thereof.

Implementation 7. The method of implementation 2, wherein the one or more additional features for the therapy are non-critical features.

Implementation 8. The method of implementation 1, wherein the one or more milestones relate to user compliance with respect to usage of the device, usage of the application, or a combination thereof.

Implementation 9. The method of implementation 1, wherein the one or more milestones also apply to one or more other users, the method further comprising: comparing satisfaction of the one or more milestones associated with the incentive scheme for the user with satisfaction of the one or more milestones associated with one or more incentive schemes of one or more other users; and providing a reward to the user, at least one of the one or more other users, or a combination based on the comparison and which of the one or more milestones have been satisfied by which of the user and the one or more other users.

Implementation 10. The method of implementation 1, further comprising unlocking one or more rewards associated with one or more participating businesses for the user based on satisfaction of the at least one of the one or more milestones.

Implementation 11. A system comprising: a control system comprising one or more processors; and a memory having stored thereon machine readable instructions; wherein the control system is coupled to the memory, and the method of any one of implementations 1 to 10 is implemented when the machine executable instructions in the memory are executed by at least one of the one or more processors of the control system.

Implementation 12. A system for communicating one or more indications to a user, the system comprising a control system configured to implement the method of any one of implementations 1 to 10.

Implementation 13. A computer program product comprising instructions which, when executed by a computer, cause the computer to carry out the method of any one of implementations 1 to 10.

Implementation 14. The computer program product of implementation 13, wherein the computer program product is a non-transitory computer readable medium.

Implementation 15. A system comprising: a memory storing machine-readable instructions; and a control system including one or more processors configured to execute the machine readable instructions to: monitor use by a user of a device, of an application associated with the device, or a combination thereof, the device providing therapy to the user, and the application providing control of the device, providing information to the user related to the therapy, or a combination thereof; determine whether one or more milestones associated with an incentive scheme for the user have been satisfied by the use, the incentive scheme relating to continued provisioning of the therapy to the user by the device; and unlock functionality of the device, the application associated with the device, or a combination thereof for the user based on satisfaction of at least one of the one or more milestones.

Implementation 16. The system of implementation 15, wherein the functionality includes: i. providing more granular control of the therapy by the device, providing one or more additional features for the therapy provided by the device, or a combination thereof, ii. one or more ways of visualizing existing data on the device, on the application, or a combination thereof, iii. providing access to premium data on the device, on the application, or a combination thereof, iv. changing one or more stylistic appearances of the device, of the application, or a combination thereof; v. providing access to, control over, or a combination thereof one or more other devices through the application; vi. pairing the device with a smartphone of the user to allow the device to receive additional information from the smartphone, the information unlocking further functionality on the device; vii. providing latest news related to the device, the application, the therapy provided by the device, or a combination thereof; and/or viii. accessing software updates for the device, the application, or a combination thereof.

Implementation 17. The system of implementation 16, wherein the one or more stylistic appearances of the device include one or more stylistic appearances of a housing of the device, of a user interface of the device, or a combination thereof.

Implementation 18. The system of implementation 16, wherein the additional information from the smartphone includes Global Positioning System (GPS) information for automatically setting functionality of the device based on environmental conditions associated with the GPS information.

Implementation 19. The system of implementation 16, wherein the device does not have access to the additional information without the pairing of the device with the smartphone.

Implementation 20. The system of implementation 16, wherein the application executes on the smartphone, and the additional information includes physiological information of the user determined by the smartphone, user identification information provided by the user through the smartphone, or a combination thereof.

Implementation 21. The system of implementation 16, wherein the one or more additional features for the therapy are non-critical features.

Implementation 22. The system of implementation 15, wherein the one or more milestones relate to user compliance with respect to usage of the device, usage of the application, or a combination thereof.

Implementation 23. The system of implementation 15, wherein the one or more milestones also apply to one or more other users, and the one or more processors are configured to execute the machine-readable instructions to: compare satisfaction of the one or more milestones associated with the incentive scheme for the user with satisfaction of the one or more milestones associated with one or more incentive schemes of one or more other users; and provide a reward to the user, at least one of the one or more other users, or a combination based on the comparison and which of the one or more milestones have been satisfied by which of the user and the one or more other users.

Implementation 24. The system of implementation 15, wherein the one or more processors are configured to execute the machine-readable instructions to unlock one or more rewards associated with one or more participating businesses for the user based on satisfaction of the at least one of the one or more milestones.

One or more elements or aspects or steps, or any portion(s) thereof, from one or more of any of the above implementations above can be combined with one or more elements or aspects or steps, or any portion(s) thereof, from one or more of any of the other above implementations or combinations thereof, to form one or more additional implementations and/or claims of the present disclosure.

While the present disclosure has been described with reference to one or more particular embodiments or implementations, those skilled in the art will recognize that many changes may be made thereto without departing from the spirit and scope of the present disclosure. Each of these implementations and obvious variations thereof is contemplated as falling within the spirit and scope of the present disclosure. It is also contemplated that additional implementations according to aspects of the present disclosure may combine any number of features from any of the implementations described herein.

What is claimed is:

1. A method comprising:
monitoring use by a user of a device, of an application associated with the device, or a combination thereof, the device providing therapy to the user, and the application providing control of the device, providing information to the user related to the therapy, or a combination thereof;
determining, based on the use by the user of the device, of the application associated with the device, or a combination thereof, that the user is at risk of losing interest in the therapy, the application, or a combination thereof;
determining whether one or more milestones associated with an incentive scheme for the user have been satisfied by the use, the incentive scheme relating to continued provisioning of the therapy to the user by the device; and
unlocking functionality of the device, the application associated with the device, or a combination thereof for the user based on satisfaction of at least one of the one or more milestones.

2. The method of claim 1, wherein the functionality includes:
i. providing more granular control of the therapy by the device, providing one or more additional features for the therapy provided by the device, or a combination thereof;
ii. one or more ways of visualizing existing data on the device, on the application, or a combination thereof;
iii. providing access to premium data on the device, on the application, or a combination thereof;
iv. changing one or more stylistic appearances of the device, of the application, or a combination thereof;
v. providing access to, control over, or a combination thereof one or more other devices through the application;
vi. pairing the device with a smartphone of the user to allow the device to receive additional information from the smartphone, the information unlocking further functionality on the device;
vii. providing latest news related to the device, the application, the therapy provided by the device, or a combination thereof; and/or
viii. accessing software updates for the device, the application, or a combination thereof.

3. The method of claim 2, wherein the one or more stylistic appearances of the device include one or more stylistic appearances of a housing of the device, of a user interface of the device, or a combination thereof.

4. The method of claim 2, wherein the additional information from the smartphone includes Global Positioning System (GPS) information for automatically setting functionality of the device based on environmental conditions associated with the GPS information.

5. The method of claim 2, wherein the device does not have access to the additional information without the pairing of the device with the smartphone.

6. The method of claim 2, wherein the application executes on the smartphone, and the additional information includes physiological information of the user determined by the smartphone, user identification information provided by the user through the smartphone, or a combination thereof.

7. The method of claim 2, wherein the one or more additional features for the therapy are non-critical features.

8. The method of claim 1, wherein the one or more milestones relate to user compliance with respect to usage of the device, usage of the application, or a combination thereof.

9. The method of claim 1, wherein the one or more milestones also apply to one or more other users, the method further comprising:
comparing satisfaction of the one or more milestones associated with the incentive scheme for the user with satisfaction of the one or more milestones associated with one or more incentive schemes of one or more other users; and providing a reward to the user, at least one of the one or more other users, or a combination based on the comparison and which of the one or more milestones have been satisfied by which of the user and the one or more other users.

10. The method of claim 1, further comprising unlocking one or more rewards associated with one or more participating businesses for the user based on satisfaction of the at least one of the one or more milestones.

11. A system comprising:

a memory storing machine-readable instructions; and a control system including one or more processors configured to execute the machine readable instructions to:

monitor use by a user of a device, of an application associated with the device, or a combination thereof, the device providing therapy to the user, and the application providing control of the device, providing information to the user related to the therapy, or a combination thereof;

determine, based on the use by the user of the device, of the application associated with the device, or a combination thereof, that the user is at risk of losing interest in the therapy, the application, or a combination thereof determine whether one or more milestones associated with an incentive scheme for the user have been satisfied by the use, the incentive scheme relating to continued provisioning of the therapy to the user by the device; and unlock functionality of the device, the application associated with the device, or a combination thereof for the user based on satisfaction of at least one of the one or more milestones.

12. The system of claim 11, wherein the functionality includes:

i. providing more granular control of the therapy by the device, providing one or more additional features for the therapy provided by the device, or a combination thereof;

ii. one or more ways of visualizing existing data on the device, on the application, or a combination thereof;

iii. providing access to premium data on the device, on the application, or a combination thereof;

iv. changing one or more stylistic appearances of the device, of the application, or a combination thereof;

v. providing access to, control over, or a combination thereof one or more other devices through the application;

vi. pairing the device with a smartphone of the user to allow the device to receive additional information from the smartphone, the information unlocking further functionality on the device;

vii. providing latest news related to the device, the application, the therapy provided by the device, or a combination thereof, and/or viii. accessing software updates for the device, the application, or a combination thereof.

13. The system of claim 12, wherein the one or more stylistic appearances of the device include one or more stylistic appearances of a housing of the device, of a user interface of the device, or a combination thereof.

14. The system of claim 12, wherein the additional information from the smartphone includes Global Positioning System (GPS) information for automatically setting functionality of the device based on environmental conditions associated with the GPS information.

15. The system of claim 12, wherein the device does not have access to the additional information without the pairing of the device with the smartphone.

16. The system of claim 12, wherein the application executes on the smartphone, and the additional information includes physiological information of the user determined by the smartphone, user identification information provided by the user through the smartphone, or a combination thereof.

17. The system of claim 12, wherein the one or more additional features for the therapy are non-critical features.

18. The system of claim 11, wherein the one or more milestones relate to user compliance with respect to usage of the device, usage of the application, or a combination thereof.

19. The system of claim 11, wherein the one or more milestones also apply to one or more other users, and the one or more processors are configured to execute the machine-readable instructions to:

compare satisfaction of the one or more milestones associated with the incentive scheme for the user with satisfaction of the one or more milestones associated with one or more incentive schemes of one or more other users; and provide a reward to the user, at least one of the one or more other users, or a combination based on the comparison and which of the one or more milestones have been satisfied by which of the user and the one or more other users.

20. The system of claim 11, wherein the one or more processors are configured to execute the machine-readable instructions to unlock one or more rewards associated with one or more participating businesses for the user based on satisfaction of the at least one of the one or more milestones.

21. The method of claim 1, wherein the determining that the user is at risk of losing interest in the therapy, the application, or a combination of thereof is based on (i) usage of the device over a period of time, (ii) usage of the application associated with the device over a period time, (iii) a frequency of usage of the device, (iv) a frequency of usage of the application associated with the device, (v) a duration of usage of the device, (vi) a duration of usage of the application associated with the device, (vii) a consistency of usage of the device, (viii) a consistency of usage of the application associated with the device, or (ix) any combination of (i)-(viii).

22. The system of claim 11, wherein the determining that the user is at risk of losing interest in the therapy, the application, or a combination of thereof is based on (i) usage of the device over a period of time, (ii) usage of the application associated with the device over a period time, (iii) a frequency of usage of the device, (iv) a frequency of usage of the application associated with the device, (v) a duration of usage of the device, (vi) a duration of usage of the application associated with the device, (vii) a consistency of usage of the device, (viii) a consistency of usage of the application associated with the device, or (ix) any combination of (i)-(viii).

* * * * *